(12) United States Patent
Kataoka et al.

(10) Patent No.: US 8,349,256 B2
(45) Date of Patent: Jan. 8, 2013

(54) BLOOD CELL ANALYZER, BLOOD CELL ANALYZING METHOD, AND COMPUTER PROGRAM PRODUCT

(75) Inventors: Hiromi Kataoka, Kochi (JP); Shoichiro Asada, Akashi (JP); Tetsuro Sugiura, Kochi (JP)

(73) Assignee: Sysmex Corporation, Kobe (JP)

( * ) Notice: Subject to any disclaimer, the term of this patent is extended or adjusted under 35 U.S.C. 154(b) by 323 days.

(21) Appl. No.: 12/622,804

(22) Filed: Nov. 20, 2009

(65) Prior Publication Data
US 2010/0129855 A1 May 27, 2010

(30) Foreign Application Priority Data

Nov. 21, 2008 (JP) .................................. 2008-297695
Nov. 21, 2008 (JP) .................................. 2008-297696

(51) Int. Cl.
*G01N 21/00* (2006.01)
*G01N 31/00* (2006.01)
*G01N 33/00* (2006.01)
*G01N 35/00* (2006.01)

(52) U.S. Cl. ........... 422/67; 422/73; 422/82.05; 436/10; 436/43

(58) Field of Classification Search .................. None
See application file for complete search history.

(56) References Cited

U.S. PATENT DOCUMENTS

| 5,047,963 A | 9/1991 | Kosaka |
| 5,050,987 A | 9/1991 | Kosaka |
| 6,842,233 B2 | 1/2005 | Narisada et al. |
| 2007/0133855 A1 | 6/2007 | Kataoka |
| 2010/0098705 A1* | 4/2010 | Eugen-Olsen et al. .... 424/143.1 |

FOREIGN PATENT DOCUMENTS

| JP | 09-27041 | 10/1997 |
| JP | 2006-091024 | 4/2006 |

OTHER PUBLICATIONS

Bickel et al. "Relation of Markers of Inflammation (C-reactive Protein, Fibrinogen, von Willebrand Factor, and Leukocyte Count) and Statin Therapy to Long-Term Mortality in Patients With Angiographically Proven Coronary Artery Disease" The American Journal of Cardiology. vol. 89, Issue 8, pp. 901-908, Apr. 15, 2002.*

* cited by examiner

*Primary Examiner* — Jill Warden
*Assistant Examiner* — Charles D Hammond
(74) *Attorney, Agent, or Firm* — Brinks Hofer Gilson & Lione

(57) ABSTRACT

A blood cell analyzer comprising: a detector for detecting predetermined component of leukocytes contained in a specimen; and a controller, including a memory under the control of a processor, the memory storing: correlation information relating to the correlation between leukocyte distribution data and either stab neutrophil or segmented leukocyte classification data; and instructions enabling the processor to carry out operations, comprising: (a) obtaining leukocyte distribution data of a subject based on the detection results of the detector; (b) obtaining the stab neutrophil or segmented leukocyte classification data based on the correlation information and the leukocyte distribution data of the subject; and (c) outputting the obtained stab neutrophil or segmented leukocyte classification data. A blood cell analyzing method and a computer program product is also disclosed.

12 Claims, 21 Drawing Sheets

(a)

(b)

(a)

(b)

BLOOD CELL ANALYZER, BLOOD CELL ANALYZING METHOD, AND COMPUTER PROGRAM PRODUCT

RELATED APPLICATIONS

This application claims priority under 35 U.S.C. §119 to Japanese Patent Application Nos. JP2008-297695 and JP2008-297696 both filed on Nov. 21, 2008, the entire content of which is hereby incorporated by reference.

FIELD OF THE INVENTION

The present invention relates to a blood cell analyzer, blood cell analyzing method, and computer program product.

BACKGROUND

Normal peripheral blood usually contains five types of leukocytes, that is, lymphocytes, monocytes, eosinophils, neutrophils, and basophils, in predetermined ratios. Whether the ratios of these components present in the blood are normal can be determined by counting and classifying the leukocytes in the blood.

When disease is present, various phenomena arise such as the classification ratios of the leukocytes change and abnormal cells appear. For example, when an inflammatory response occurs in vivo due to bacterial infection or the like, there is an increase in the ratio of immature leukocytes and there are also increases of stab neutrophils with unlobed nuclei and segmented cells with few segmented nuclei. Effective information for determining whether disease is present can therefore be obtained by classifying and counting leukocytes.

For example, Japanese Laid-Open Patent Publication No. 2006-91024 and U.S. Pat. No. 6,842,233 disclose methods for classifying and counting normal leukocytes and classifying and counting immature leukocytes. U.S. Pat. No. 5,050,987 and U.S. Pat. No. 5,047,963 disclose particle analyzers for extracting the complexity of the particle signals of a leukocyte and determining the number of lobes of a nucleus. Japanese Laid-Open Patent Publication No. 9-274041 discloses a method for measuring CRP concentration in blood without centrifuging the collected blood. United States Patent Publication No. 2007/0133855 discloses a pattern-matching apparatus capable of searching similarities in leukocyte particle patterns.

The methods disclosed in Japanese Laid-Open Patent Publication No. 2006-91024 and U.S. Pat. No. 6,842,233, however, require a device for classifying and counting normal leukocytes and a separate device for classifying and counting immature leukocytes. The analyzers disclosed in U.S. Pat. Nos. 5,050,987 and 5,047,963 require complex signal processing, both blood analyzers have complicated structures that are difficult to make more compact and light weight, and are difficult to make less expensive. Japanese Laid-Open Patent Publication No. 9-274041 also requires a device for counting normal leukocytes, and measuring CRP by a special immunological measuring method that requires reagents and devices. Of course, CRP measurement and leukocyte measurement can be performed by commercial apparatuses, but the aspect of requiring immunological reagents for the CRP measurement remains unchanged.

SUMMARY OF THE INVENTION

A first aspect of the present invention is a blood cell analyzer comprising: a detector for detecting predetermined component of leukocytes contained in a specimen; and a controller, including a memory under the control of a processor, the memory storing: correlation information relating to the correlation between leukocyte distribution data and either stab neutrophil or segmented leukocyte classification data; and instructions enabling the processor to carry out operations, comprising:
(a) obtaining leukocyte distribution data of a subject based on the detection results of the detector; (b) obtaining the stab neutrophil or segmented leukocyte classification data based on the correlation information and the leukocyte distribution data of the subject; and (c) outputting the obtained stab neutrophil or segmented leukocyte classification data.

A second aspect of the present invention is a blood cell analyzer comprising: a detector for detecting predetermined component of leukocytes contained in a specimen; and a controller, including a memory under the control of a processor, the memory storing: correlation information relating to the correlation between inflammation-related marker measurement data and leukocyte distribution data; and instructions enabling the processor to carry out operations, comprising: (a) obtaining leukocyte distribution data of a subject based on the detection results of the detector; (b) obtaining the inflammation-related marker measurement data based on the correlation information and the leukocyte distribution data of the subject; and (c) outputting the obtained inflammation-related marker measurement data.

A third aspect of the present invention is a blood cell analyzing method comprising: (a) obtaining leukocyte distribution data of a subject based on detection results of a detector; (b) obtaining stab neutrophil or segmented leukocyte classification data based on correlation information and the leukocyte distribution data of the subject; and (c) outputting the obtained stab neutrophil or segmented leukocyte classification data.

A forth aspect of the present invention is a blood cell analyzing method comprising: (a) obtaining leukocyte distribution data of a subject based on detection results of a detector; (b) obtaining inflammation-related marker measurement data based on the correlation information and the leukocyte distribution data of the subject; and (c) outputting the obtained inflammation-related marker measurement data.

A fifth aspect of the present invention is a computer program product, comprising: a computer readable medium; and instructions, on the computer readable medium, adapted to enable a general purpose computer to perform operations, comprising: (a) obtaining leukocyte distribution data of a subject based on a detection results of a detector; (b) obtaining stab neutrophil or segmented leukocyte classification data based on correlation information and leukocyte distribution data of the subject; and (c) outputting the obtained stab neutrophil or segmented leukocyte classification data.

A sixth aspect of the present invention is a computer program product, comprising: a computer readable medium; and instructions, on the computer readable medium, adapted to enable a general purpose computer to perform operations, comprising: (a) obtaining leukocyte distribution data of a subject based on the detection results of the detector; (b) obtaining inflammation-related marker measurement data based on the correlation information and leukocyte distribution data of the subject; and (c) outputting the obtained inflammation-related marker measurement data.

DETAILED DESCRIPTION OF THE PREFERRED EMBODIMENTS

The embodiments are described hereinafter by way of example of a blood cell analyzer for performing a blood classification process based on the drawings.

(First Embodiment)

Figure 1:
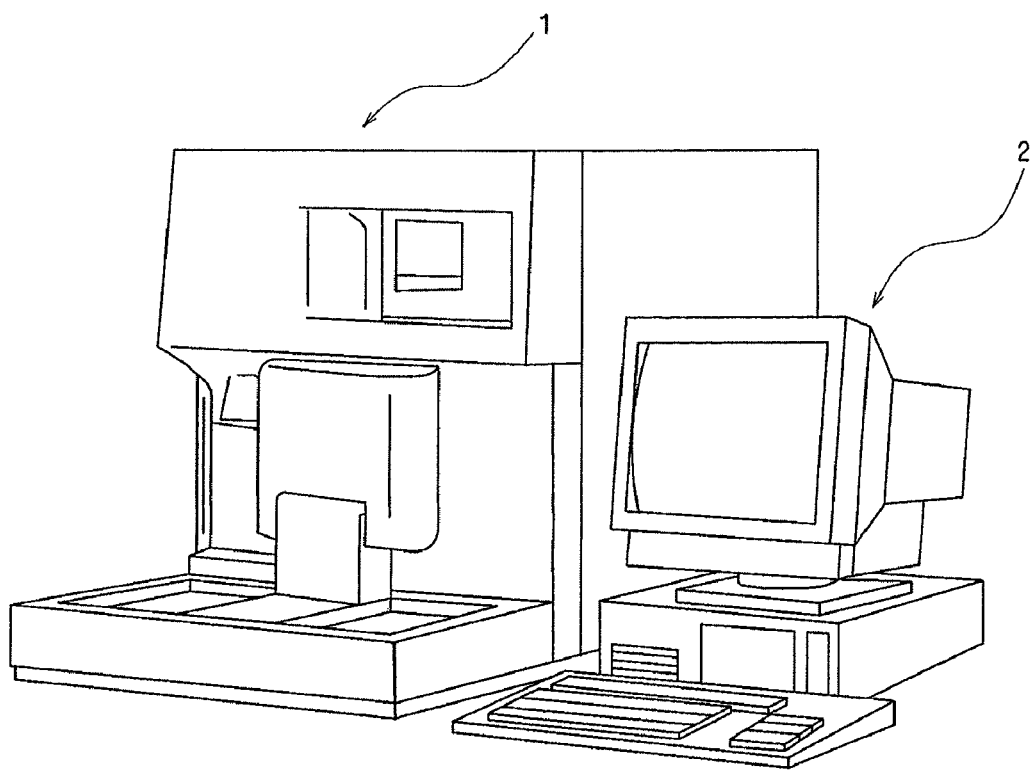
FIG. 1 is a perspective view schematically showing the structure of a first embodiment of a blood cell analyzer of the present invention.

FIG. 1 is a perspective view schematically showing the structure of a first embodiment of a blood cell analyzer of the present invention. As shown in FIG. 1, the blood cell analyzer of the first embodiment incorporates a measuring device 1 and an operation and display device 2 which are connected so as to be capable of mutually sending and receiving data.

The measuring device 1 and the operation and display device 2 are connected by a communication line which is not shown in the drawing; mutual data communication allows the operation of the measuring device 1 to be controlled, the measurement data output from the measuring device 1 to be processed, and the analysis result therefrom to be obtained. The measuring device 1 and the operation and display device 2 may also be connected through a network, or may be integratedly configured in a single apparatus to transfer data via communication during processing.

The measuring device 1 detects characteristic information of the leukocytes, reticulocytes and the like in the blood using flow cytometry, and transmits the detection results as measurement data to the operation and display device 2. Flow cytometry is a method in which the particles in a measurement sample are detected by forming a preparation containing a measurement sample into a flow, irradiating the sample flow by laser light, then detecting the forward scattered light, side scattered light, and side fluorescent light emitted from the particles (blood cells) in the measurement sample so as to detect the particles thereby.

Figure 2:
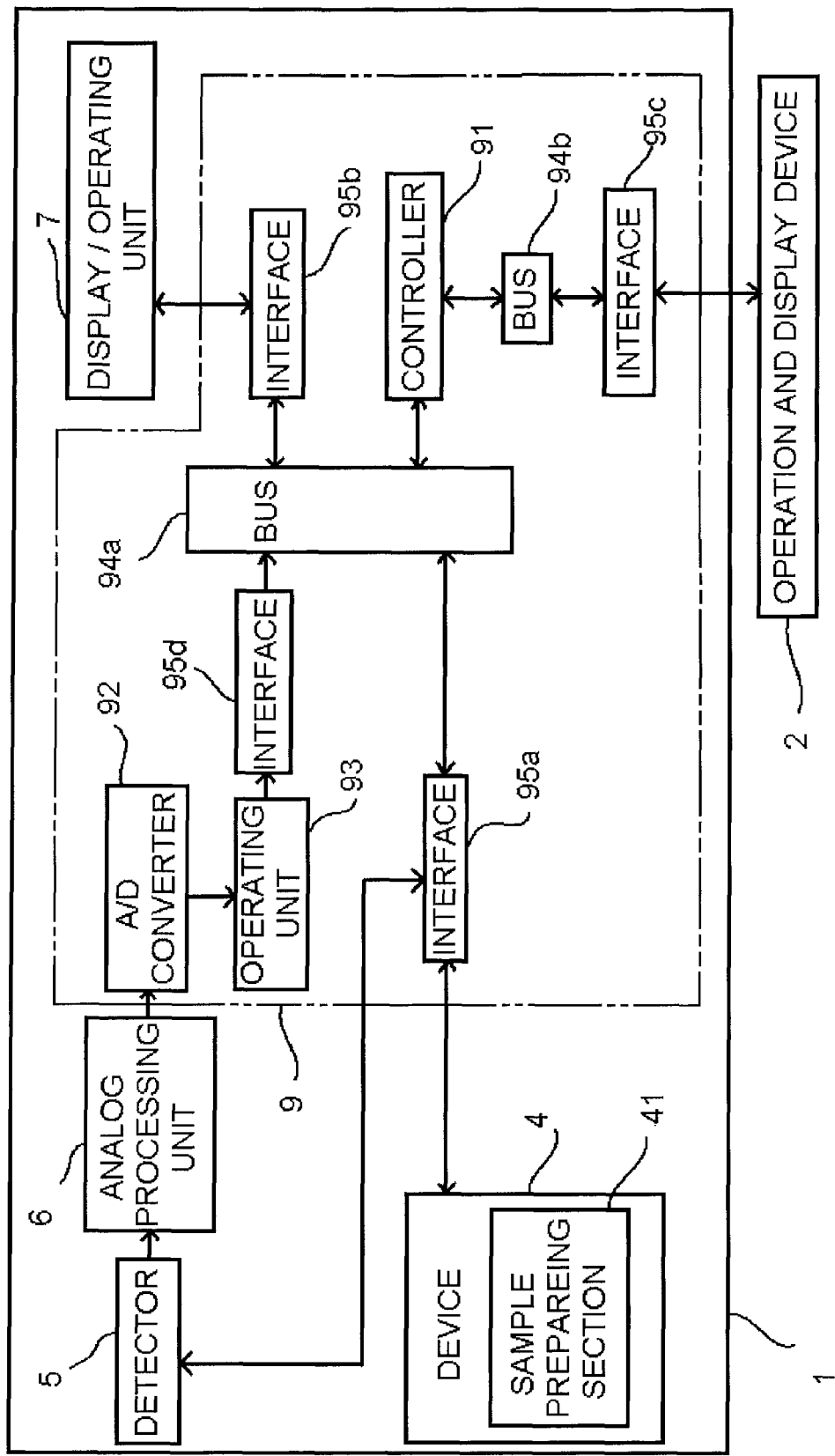
FIG. 2 is a block diagram showing the structure of the measuring device of the first embodiment of the blood cell analyzer of the present invention.

FIG. 2 is a block diagram showing the structure of the measuring device 1 of the first embodiment of the blood cell analyzer of the present invention. The measuring device 1 is configured by a device 4, detection unit 5 for performing measurements of the measurement sample, analog processing unit 6 for processing the output of the detection unit 5, display/operating unit 7, and control board 9 for controlling the operation of each of the hardware components.

The control board 9 has a controller 91 that includes a control processor and a memory for performing the operations of the control processor, a 12-bit A/D converter 92 for converting the signals output from the analog processing unit 6 into digital signals, and an operation unit 93 for storing the digital signals output from the A/D converter 92 and executing processing of the data output from the controller 91. The controller 91 is connected to the display/operating unit 7 through a bus 94a and an interface 95b, and connected the operation and display device 2 through a bus 94b and an interface 95c. The operation unit 93 outputs the operation result to the controller 91 through an interface 95d and a bus 94a. The controller 91 also transmits the operation results (measurement data) operation and display device 2.

The device 4 is provided with a sample preparing section 41 for preparing a measurement sample from blood and reagent. The sample preparing section 41 prepares leukocyte measurement samples, reticulocyte measurement samples, and platelet measurement samples.

Figure 3:
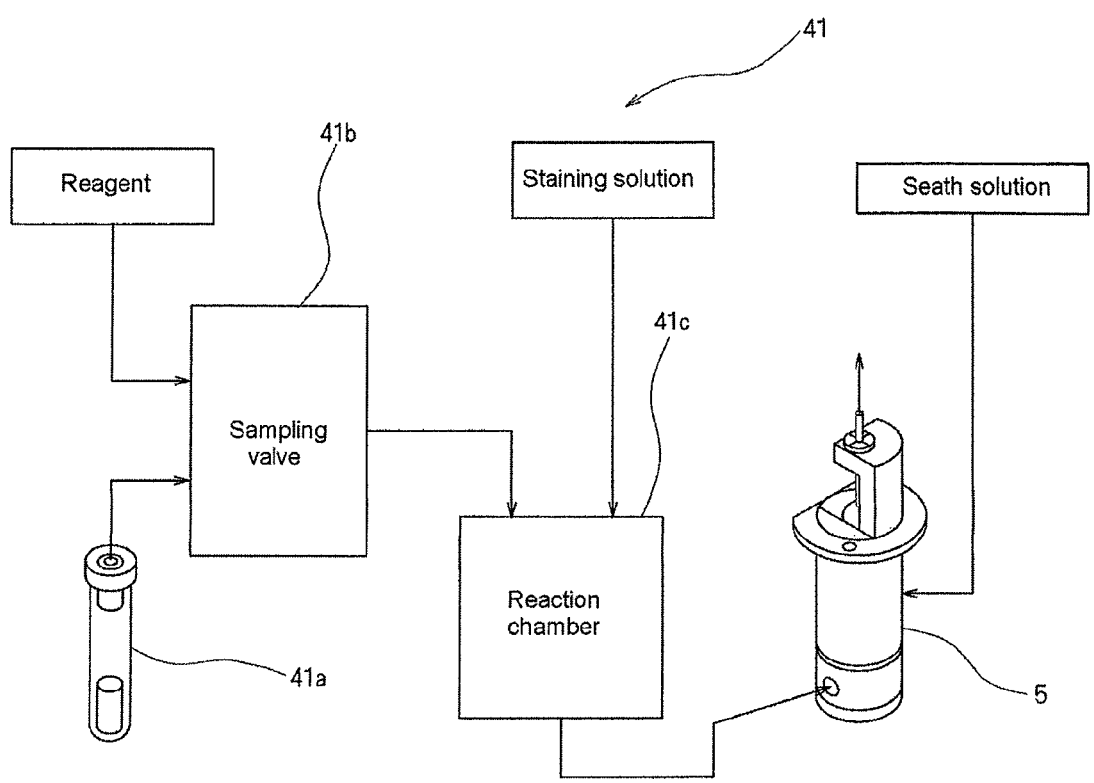
FIG. 3 is a block diagram schematically showing the structure of sample preparing section of the first embodiment of the present invention.

FIG. 3 is a block diagram schematically showing the structure of sample preparing section 41 of the first embodiment of the present invention. The sample preparing section 41 is provided with a blood collection tube 41a filled with a predetermined amount of blood, sampling valve 41b for aspirating the blood, and reaction chamber 41c.

The sampling valve 41b is configured to aspirate a predetermined amount of blood from within the blood collection tube 41a, into which the blood was previously aspirated by an aspirating pipette that is not shown in the drawing. The reaction chamber 41c is connected to the sampling valve 41b, and is used to mix predetermined amounts of reagent and staining solution with the blood measured out by the sampling valve 41b. The reaction chamber 41c is also connected to the detection unit 5, and is configured so that the measurement sample produced by mixing the predetermined amounts of reagent and staining solution in the reaction chamber 41c can flow to the detection section 5.

In this way the sample preparing section 41 can prepare a measurement sample in which the leukocytes are stained and the erythrocytes are hemolyzed as a leukocyte measurement sample. The sample preparing section 41 can also prepare a measurement sample in which the reticulocytes are stained as a reticulocyte measurement sample. The sample preparing section 41 can further prepare a measurement sample in which platelets are stained as a platelet measurement sample. The prepared measurement sample is supplied together with a sheath fluid to the sheath flow cell of the detection unit 5.

Figure 4:
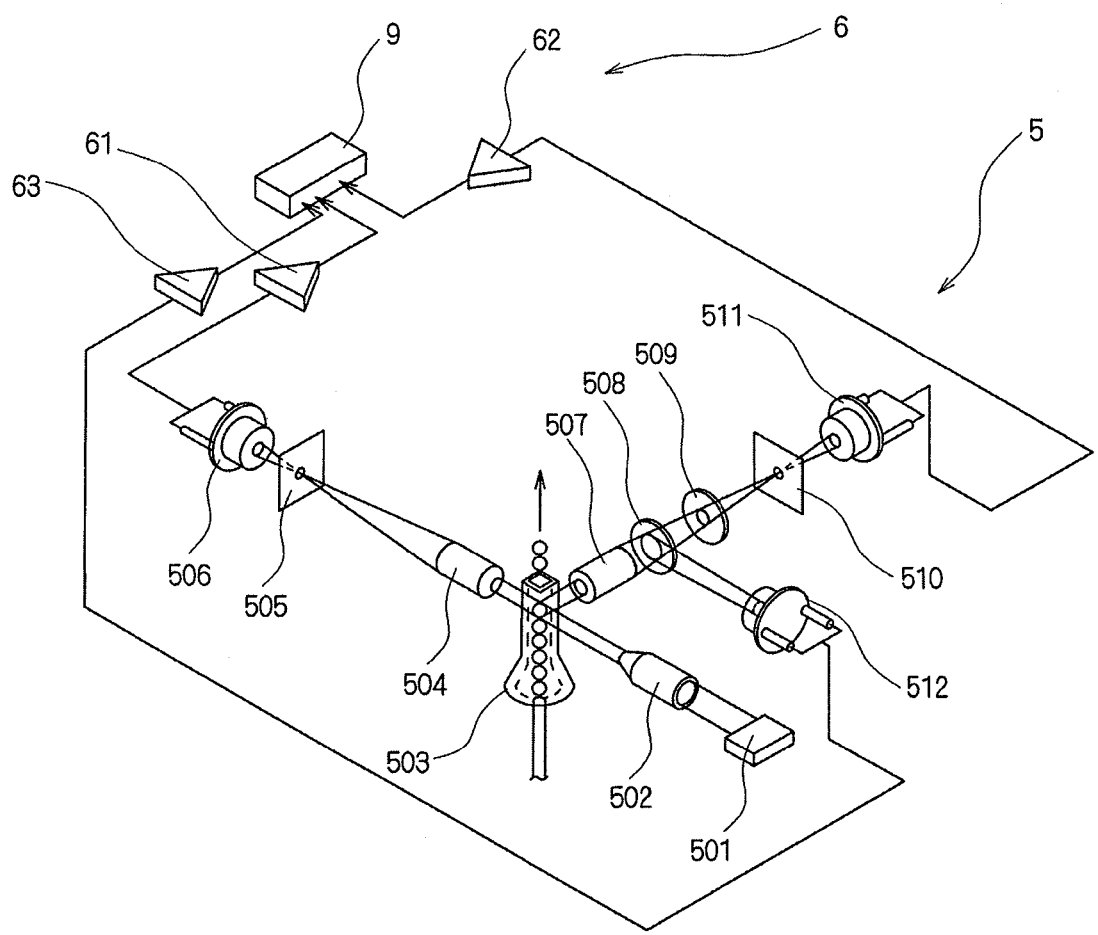
FIG. 4 is a block diagram schematically showing the structure of the detection section and analog processing section of the first embodiment of the present invention.

FIG. 4 is a block diagram schematically showing the structure of detection unit 5 and the analog processing unit 6 of the first embodiment of the present invention. As shown in FIG. 4, the detection unit 5 includes a light emitter 501 for emitting laser light, irradiation lens unit 502, sheath flow cell 503 which is irradiated by the laser light, collective lens 504 disposed on a line extending in the direction of travel of the laser light emitted from the light emitter 501, pinhole 505 and PD (photodiode) 506 (a beam stopper that is not shown in the drawing is disposed between the sheath flow cell 503 and the collective lens 504), collective lens 507 disposed in a direction intersecting the direction of travel of the light emitted from the light emitter 501, dichroic mirror 508, optical filter 509, pinhole 510 and APD (avalanche photodiode) 511, and PD (photodiode) 512 disposed on the side of the dichroic mirror 508.

The light emitter 501 is provided to emit light toward the measurement sample passing through within the sheath flow cell 503. The irradiation lens unit 502 is provided to irradiate the measurement sample with the light emitted form the light emitter 501. The PD 506 is provided to receive the forward scattered light emitted from the sheath flow cell 503. Note that information relating to the size of the particles (blood cells) in the measurement sample can be obtained from the forward scattered light emitted from the sheath flow cell 503.

The dichroic mirror 508 is provided to separate the side fluorescent light and the side scattered light emitted from the sheath flow cell 503. Specifically, the dichroic mirror is provided to direct the side scattered light emitted from the sheath flow cell 503 into the PD 512, and direct the side fluorescent light emitted from the sheath flow cell 503 into the APD 511. The PD 512 is provided to receive the side scattered light. Information relating to the interior of the particle (blood cell) in the measurement sample, such as the size of the nucleus, can be obtained from the side scattered light emitted from the sheath flow cell 503.

The APD 511 is provided to receive the side fluorescent light. When a fluorescent substance such as a stained blood cell is irradiated with light, light is generated which has a longer wavelength than the wavelength of the irradiating light. The intensity of the side fluorescent light increases as the degree of staining increases. Therefore, characteristic information relating to the degree of staining of the blood cell can be obtained by measuring the intensity of the side fluorescent light emitted from the sheath flow cell 503. Other measurements can be performed, such as classifying leukocytes, on the difference in the intensities of the side fluorescent light. The PDs 506 and 512, and the APD 511 convert the respective light signals to electrical signals, which are then amplified by the amplifiers 61, 62, and 63 and transmitted to the control board 9.

Figure 5:
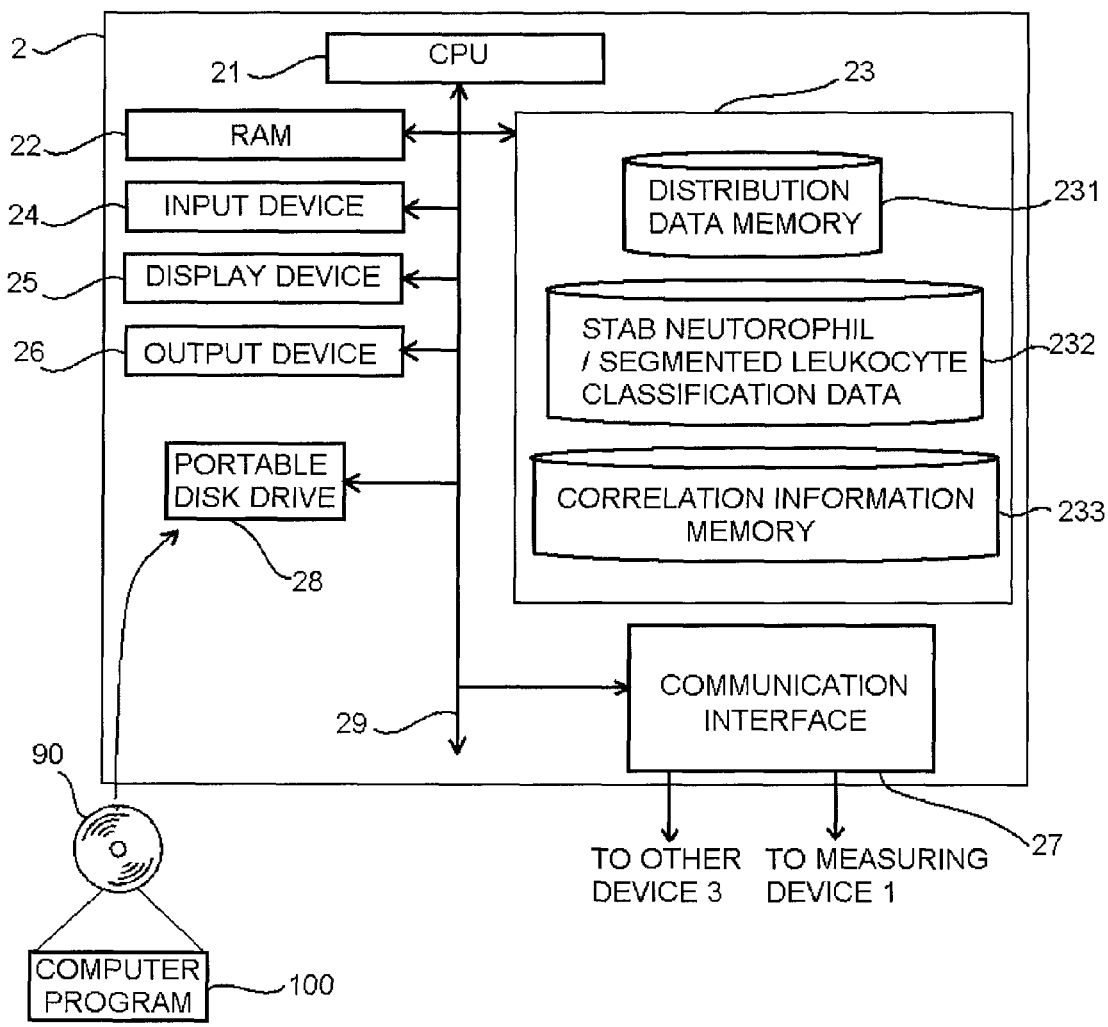
FIG. 5 is a block diagram showing the structure of the operation and display device of the first embodiment of the blood cell analyzer of the present invention.

FIG. 5 is a block diagram showing the structure of the operation and display device 2 of the first embodiment of the blood cell analyzer of the present invention. The operation and display device 2 has the function of obtaining correlation information relating to the correlation between the stab neutrophil or the segmented leukocyte classification data and the leukocyte distribution data, in addition to the functions of the operation and display device of a conventional blood cell analyzer. As shown in FIG. 5, the operation and display device 2 is configured by a CPU (central processing unit) 21, RAM 22, memory device 23, input device 24, display device 25, output device 26, communication interface 27, portable disk drive 28, and an internal bus 29 which connects all these hardware components. The CPU 21 is connected to each described hardware component of the operation and display device 2 via the internal bus 29, and executes the various software functions according to a computer program 100 stored in the memory device 23. The RAM 22 is configured by a volatile memory such as SRAM, SDRAM or the like, and is used to develop the load module during the execution of the computer program 100, and to store the temporary data generated during the execution of the computer program 100.

The memory device 23 is configured by an internal fixed storage device (hard disk), a volatile memory such as SRAM or the like, or a nonvolatile memory such as a ROM or the like. The computer program 100 stored in the memory device 23 is downloaded by the portable disk drive 28 from a portable recording medium 90 such as a DVD, CD-ROM or the like on which information such as programs and data are recorded, and developed from the memory device 23 to the RAM 22 during execution. Of course, the computer program may also be downloaded from an external computer connected to the network via the communication interface 27.

The memory device 23 is an internal fixed storage device (hard disk) or the like. The memory device 23 includes a distribution data memory 231 for storing the leukocyte distribution data obtained by the measuring device 1, stab neutrophil/segmented leukocyte classification data memory 232 for storing stab neutrophil or segmented leukocyte classification data obtained by the other detection device 3, and a correlation information memory 233 for storing correlation information relating to correlation relationships. The CPU 21 calculates the correlation information for estimating the classification data of the stab neutrophils or segmented leukocytes from the leukocyte distribution information by analyzing the classification data of the stab neutrophils or segmented leukocytes and the leukocyte distribution data respectively stored in the stab neutrophil/segmented leukocyte classification data memory 232 and the distribution data memory 231. Note that the distribution data memory 231, stab neutrophil/segmented leukocyte classification data memory 232, and correlation information memory 233 are not limited to being provided in the memory device 23, and may be pre-stored in an external computer so that the information can be obtained through the communication interface 27. The correlation information may also be calculated by an external computer similarly provided with an operation and display device 2, and the calculated correlation information may also be pre-stored in the correlation information memory 233 of the memory device 23. In this case, the classification data and distribution data required for the calculation of the correlation information need not be stored in the memory device 23 of the operation and display device 2, and the correlation information calculation process performed by the CPU 21 may be omitted.

The communication interface 27 is connected to the internal bus 29 so that data can be sent and received to the measuring device 1 via the connected communication line. That is, instruction information specifying to start a measurement and the like can be transmitted to the measuring device 1, and the measurement data and the like can be received.

The input device 24 is a data input medium such as a keyboard and mouse. The display device 25 is a CRT, LCD or the like for displaying the analysis results. The output device 26 is a printing device such as a laser printer, inkjet printer or the like.

Figure 6:
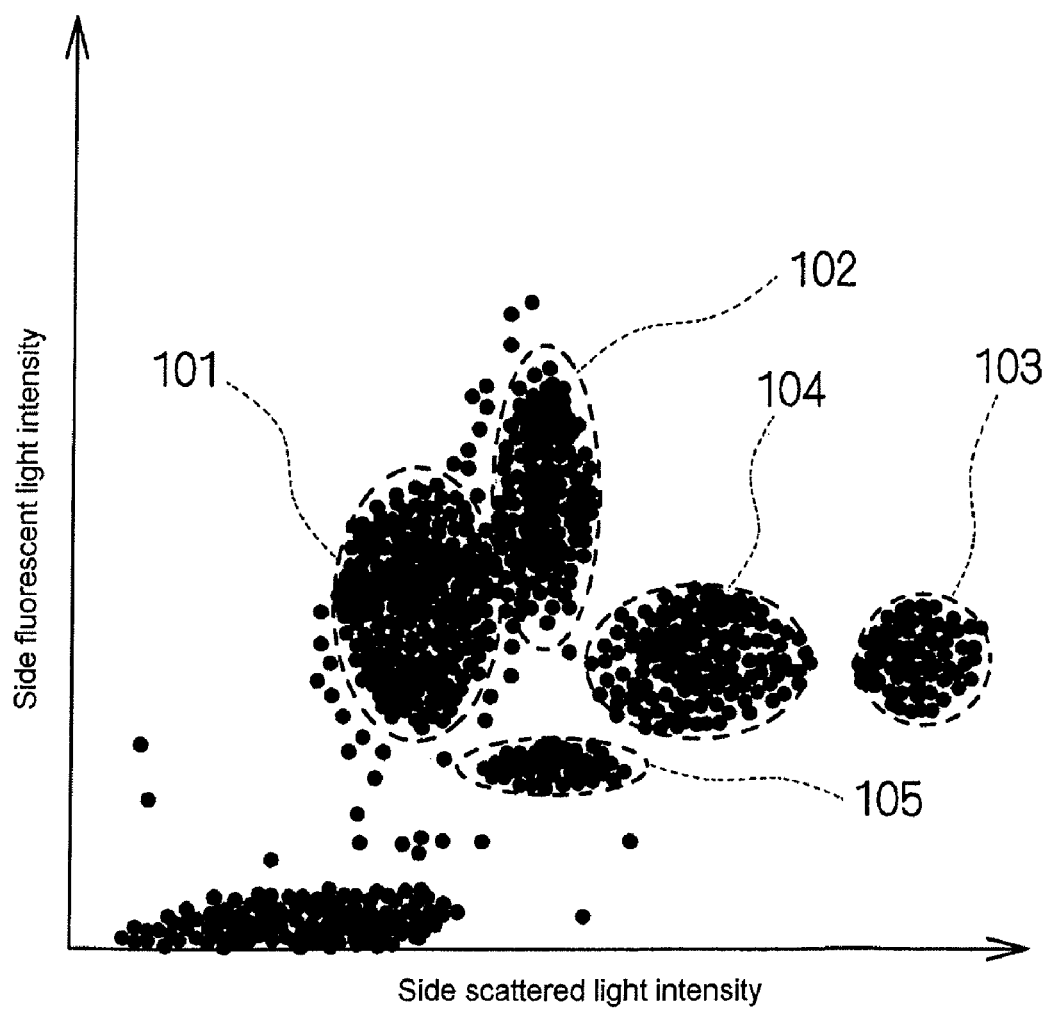
FIG. 6 shows an example of a scattergram when performing the leukocyte classification measurement (DIFF)

When the measuring device 1 and the operation and display device 2 of the blood cell analyzer of the above described structure measures the blood of a patient and has classified the leukocytes contained in the blood into lymphocytes, monocytes, eosinophils, neutrophils, basophils, a scattergram such as the one shown in FIG. 6 is prepared and displayed on the display device 25. FIG. 6 shows an example of a scattergram when performing the leukocyte classification measurement (DIFF). In FIG. 6, the side fluorescent light intensity is plotted on the vertical axis and the side scattered light intensity is plotted on the horizontal axis. The method of classifying the leukocytes using the blood cell analyzer of the first embodiment is described below.

A scattergram such as that shown in FIG. 6 is obtainable by the blood cell analyzer of the first embodiment of the present invention. The scattergram shows a lymphocyte distribution region 101 in which particles classified as lymphocytes are distributed via clustering techniques, monocyte distribution region 102 for the distribution of monocytes, eosinophil distribution region 103 for the distribution of eosinophils, neutrophil distribution region 104 for the distribution of neutrophils, and basophil distribution region 105 for the distribution of basophils. The numbers of lymphocytes, monocytes and the like are determined by counting the classified blood cells. The classification and counting of the leukocytes is accomplished by the method disclosed in U.S. Pat. No. 5,555,196. Note that the computer program for executing this leukocyte classification method and the data used in the execution of the computer program are pre-stored in the memory device 23.

The present inventors have discovered a high correlation between the leukocyte distribution data and the distribution data of the stab neutrophils or segmented leukocytes by performing multiple regression analysis to extract the relationship between each type of disease and particle patterns of the leukocyte distribution data. The classification data of the stab neutrophils or segmented leukocytes can therefore be estimated form the leukocyte distribution data by predetermining the correspondence between the distribution data of the leukocytes analyzed by a conventional blood cell analyzer and the distribution data of either the stab neutrophils or segmented leukocytes obtained by another examination.

The sequence of determining the correlation between the leukocyte distribution data and the distribution data of the stab neutrophils or segmented leukocytes is described below. Although the operation and display device 2 of the first embodiment is described in terms of calculating the correlation information relating to the correlation, the correlation information is not limited to calculation by the operation and display device 2 inasmuch as such correlation information may be calculated by an external computer and thereafter obtained over the network or via a portable recording medium.

Figure 7:
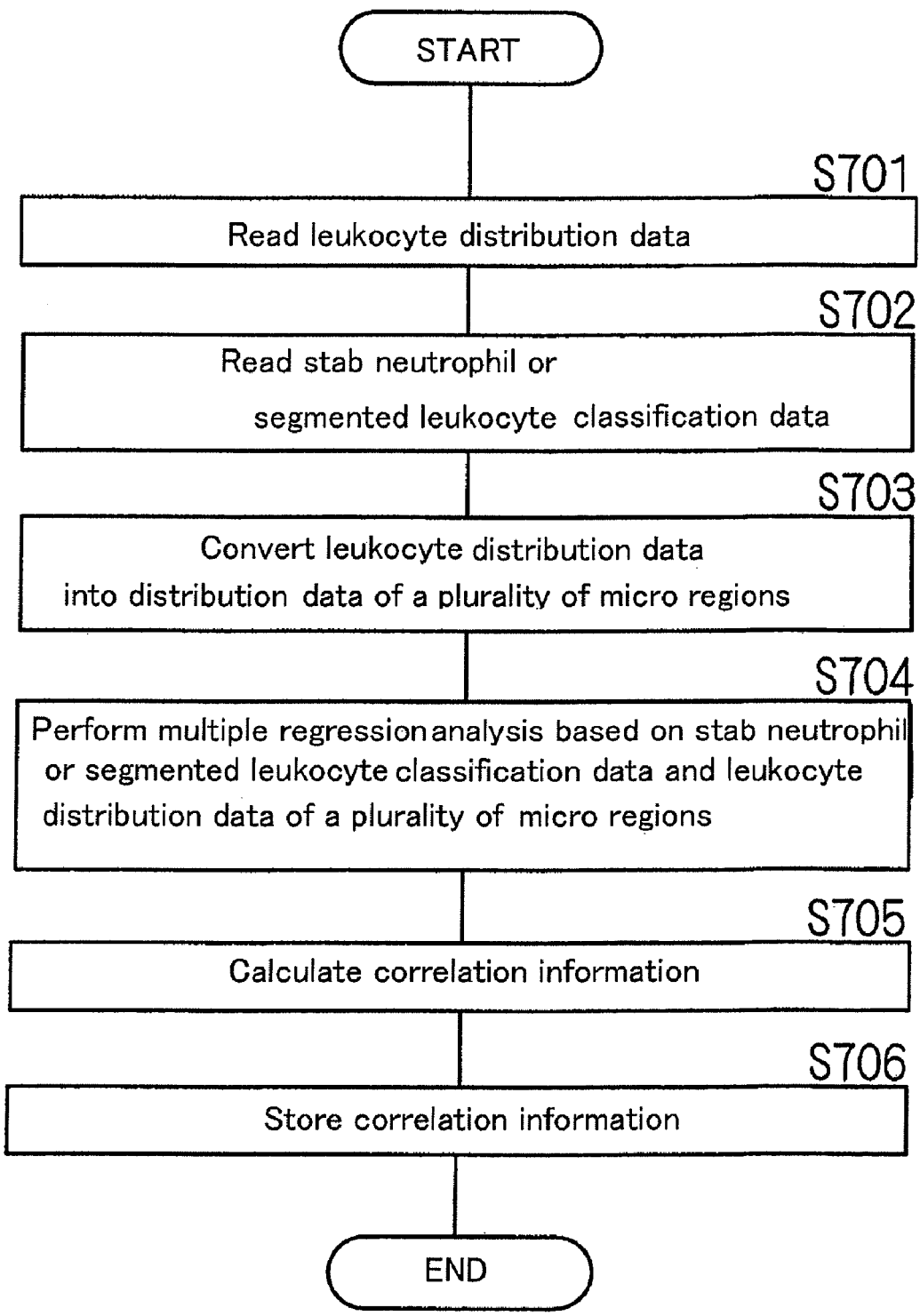
FIG. 7 is a flow chart showing the sequence of the process for calculating the correlation information relating to the correlation performed by the CPU of the operation and display device of the first embodiment of the present invention.

FIG. 7 is a flow chart showing the sequence of the process for calculating the correlation information relating to the correlation performed by the CPU 21 of the operation and display device 2 of the first embodiment of the present invention. The CPU 21 of the operation and display device 2 reads the leukocyte distribution data stored in the distribution data memory 231 of the memory device 23 (step S701).

The CPU 21 reads the distribution data of the stab neutrophils or segmented leukocytes stored in the stab neutrophil/segmented leukocyte distribution data memory 232 of the memory device 23 which has been obtained by another method, for example, microscopic observation (step S702), and calculates the correlation information relating to the relationship between the read leukocyte distribution data and the distribution data of the stab neutrophils or segmented leukocytes.

Figure 8:
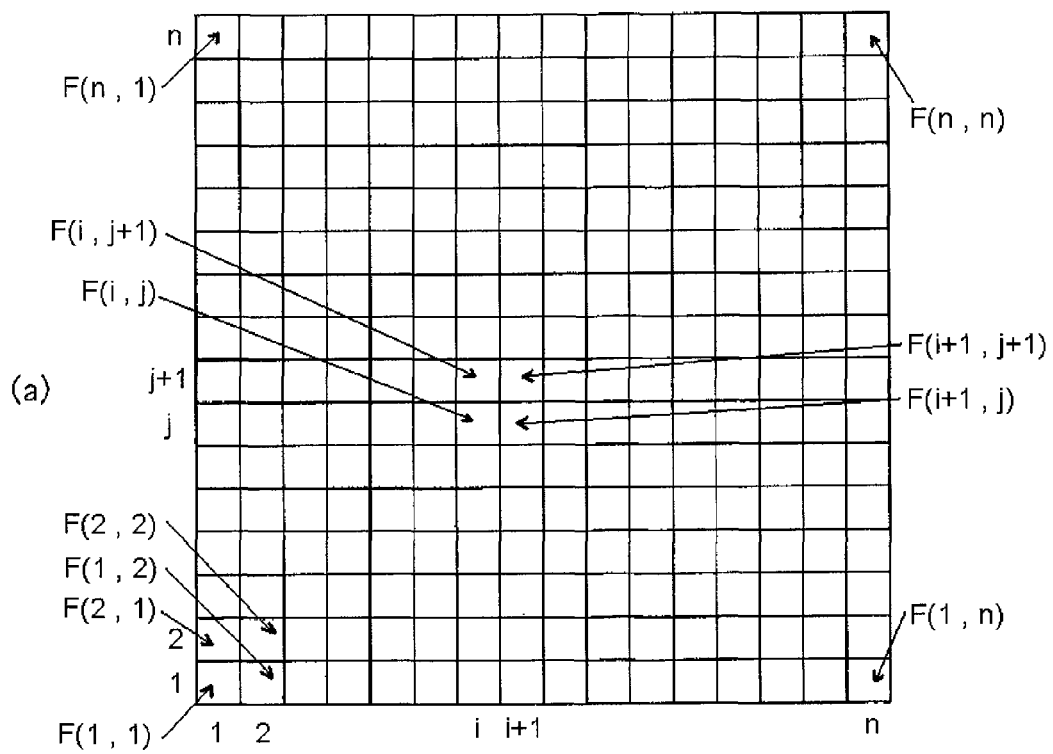
FIG. 8 illustrates the method of converting to distribution data of each micro region based on the scattergram displaying the leukocyte distribution data.
Figure 8:
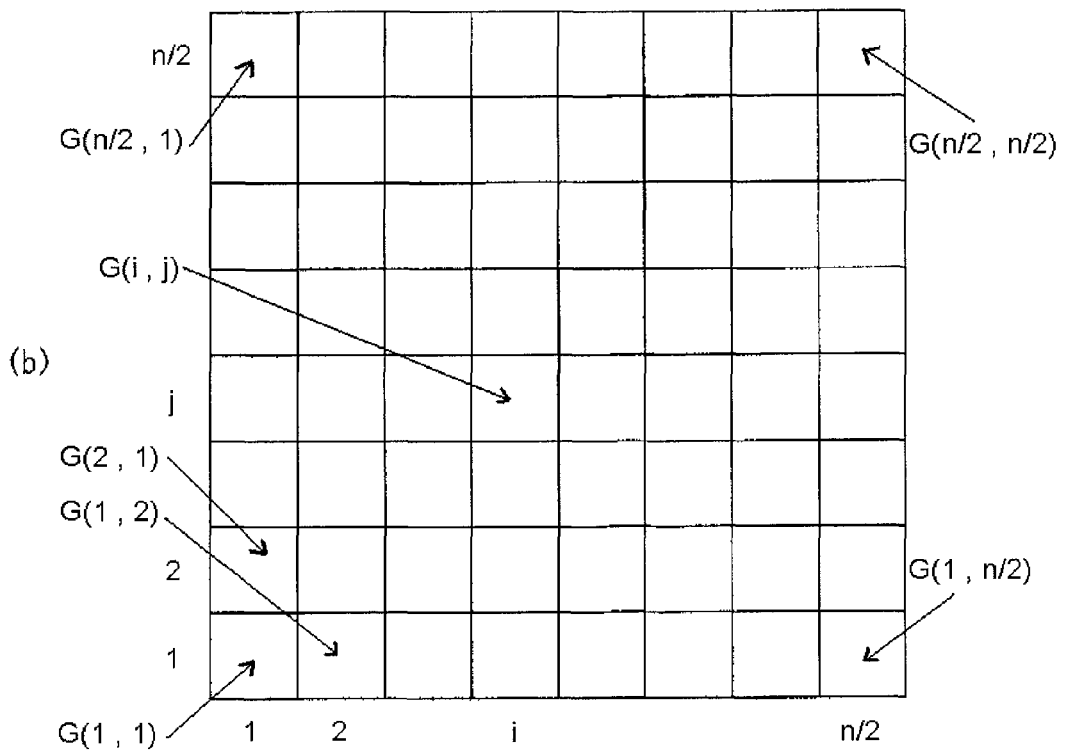

Specifically, the read leukocyte distribution data are converted to a distribution data for a plurality of micro regions (step S703), multiple regression analysis is performed based on the converted distribution data of the micro regions and the read distribution data of the stab neutrophils and segmented leukocytes (step S704), and the correlation information related to the relationship is calculated (step S705). FIG. 8 illustrates the method of converting to distribution data of each small region based on the scattergram displaying the leukocyte distribution data.

In the example of FIG. 8, a scattergram represents data groups in which a number F $(i, j)$ is allocated to each n×n (n=256) address $(i, j)$. The scattergram data may also be compressed when handling an excessive amount of data types. For example, when the addresses of the scattergram are converted so that four addresses become a single address (micro region), that is, the scattergram is compressed to n/2× n/2, a number G $(i, j)$ of the addresses of the compressed scattergram can be expressed as shown in equation (7).

$$\begin{aligned}
G(1, 1) &= F(1, 1) + F(1, 2) + F(2, 1) + F(2, 2) \quad \text{Equation (7)}\\
G(1, 2) &= F(1, 3) + F(1, 4) + F(2, 3) + F(2, 4)\\
&\vdots\\
G(i, j) &= \begin{aligned}F(2i-1, 2j-1) + \\ F(2i-1, 2j) + \\ F(2i, 2j-1) + F(2i, 2j)\end{aligned}\\
&\vdots\\
G(i, j) &= \begin{aligned}F(n-1, n-1) + \\ F(n-1, n) + \\ F(n, n-1) + F(n, n)\end{aligned}
\end{aligned}$$

For example, when an inflammation reaction occurs in vivo due to disease, the ratio of immature leukocytes increases, segmented leukocytes with few segmented nuclei and stab neutrophils with unsegmented nuclei also increase. In this way the number of data can be compressed, and correlation information can be more efficiently calculated by converting the original distribution data to distribution data of micro regions configured by four addresses.

When the 256×256 distribution data are compressed to 32×32 distribution data and subjected to multiple regression analysis, the CPU 21, as a matter of performing the multiple regression analysis process, respectively calculates the multiple regression function f of the distribution data $x_{ki}$ (i–1, 2, . . . s) of a plurality of micro regions and the classification data $A_k$ of the stab neutrophils, or the multiple regression function g of the distribution data $x_{ki}$ (i=1, 2, . . . s) of the distribution data $x_{ki}$ (i=1, 2, . . . s) of a plurality of micro regions and the segmented leukocytes, using the distribution data $x_{ki}$ (i=1, 2, . . . s) (s=1024) of a plurality of micro regions converted from the leukocyte distribution data $X_k$ (k=1, 2, . . . n) as explanatory variables, and the distribution data Bk of segmented leukocytes or obtained classification data Ak of the stab neutrophils as objective variables. When the distribution data xi has been obtained by the CPU 21 for each micro region by converted from the new leukocyte distribution data X by calculating the multiple regression analysis function for multiple regression analysis function g as the correlation information, the CPU 21 can then calculate the estimated classification data A of the stab neutrophils or the estimated classification data B of the segmented leukocytes via equation (8).

$$A = f(x1, x2, \ldots, xi, \ldots, xs)$$
$$B = g(x1, x2, \ldots, xi, \ldots, xs) \qquad \text{Eq. (8)}$$

Of course, linear multiple regression analysis may also be executed assuming the existence of a linear correlation between the obtained stab neutrophil classification data Ak or the segmented leukocyte classification data Bk and the distribution data xki (i=1, 2, . . . s) of a plurality of micro regions converted from the leukocyte distribution data Xk (k=1, 2, . . . n). In this case, the CPU 21 calculates the multiple regression functions a0, ai, b0, and bi by executing linear multiple regression analysis using the distribution data xki (i=1, 2, . . . s) of a plurality of micro regions converted from the leukocyte distribution data Xk (k=1, 2, . . . n) as explanatory variables, and the obtained stab neutrophil classification data Ak or the segmented leukocyte distribution data Bk as objective variables. When the distribution data xi has been obtained by the CPU 21 for each micro region by converted from the new leukocyte distribution data X by calculating the multiple regression analysis functions a0, ai, b0, bi as correlation information, the CPU 21 can then calculate the estimated classification data A of the stab neutrophils or the estimated classification data B of the segmented leukocytes via equation (9).

$$A = \sum_{i=1}^{s} ai \cdot xi + a0 \qquad \text{Equation (9)}$$
$$B = \sum_{i=1}^{s} bi \cdot xi + b0$$

The CPU 21 stores the calculated correlation information in the correlation information memory 233 of the memory device 23 (step S706).

Figure 9:
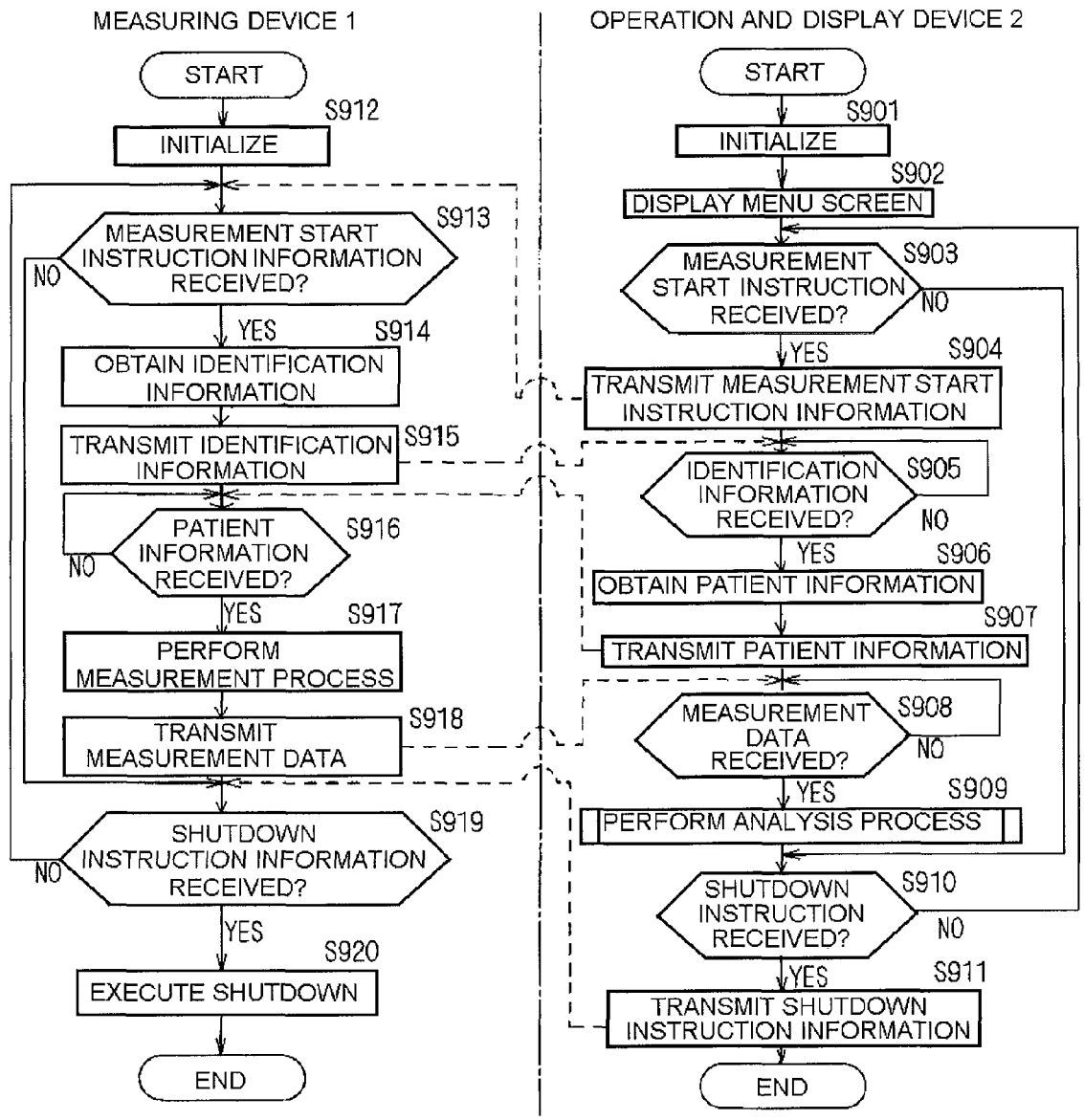
FIG. 9 is a flow chart showing the sequence of processing performed by the CPU of the operation and display device and the control unit of the control board of the measuring device of the first embodiment of the present invention.

FIG. 9 is a flow chart showing the sequence of the processes performed by the CPU 21 of the operation and display device 2, and the controller 91 of the control board 9 of the measuring device 1 of the first embodiment of the present invention. When the controller 91 of the control board 9 of the measuring device 1 detects that the measuring device 1 has been turned on, the controller 91 executes initialization (step S912), and performs an operations check of each component of the measuring device 1. The CPU 21 of the operation and display device 2 also executes initialization (program initialization) (step S901) and displays a menu screen on the display device 25 (step S902) when the CPU 21 detects that the operation and display device 2 has been turned on. The menu screen receives the selection of DIFF measurement, RET measurement, or CBC measurement, and receives the measurement start instruction and shutdown instruction. What occurs when DIFF measurement has been selected on the menu screen in the first embodiment is described below.

The CPU 21 of the operation and display device 2 determines whether a measurement start instruction has been received (step S903); when the CPU 21 determines that the measurement start instruction has not been received (step S903: NO), the CPU 21 skips steps S904 through S909. When the CPU 21 determines that the measurement start instruction has been received (step S903: YES), the CPU 21 transmits instruction information indicating to start a measurement to the measuring device 1 (step S904). The controller 91 of the control board 9 of the measuring device 1 determines whether instruction information indicating to start a measurement has been received (step S913); when the controller 91 determines that the instruction information indicating to start a measurement has been received (step S913: YES), the controller 91 has the barcode reader (not shown in the drawing) read the barcode label (not shown in the drawing) adhered to the container holding the blood to obtain the blood identification information (sample ID) (step S914). When the controller 91 determines that the instruction information indicating to start a measurement has not been received (step S913: NO), the controller skips steps S914 through S918.

The controller 91 transmits the obtained identification information (sample ID) to the operation and display device 2 (step S915), and the CPU 21 of the operation and display device 2 determines whether the identification information (sample ID) has been received (step S905). When the CPU 21 determines that the identification information (sample ID) has not been received (step S905: NO), the CPU 21 enters a reception standby state. When the CPU 21 determines that the identification information (sample ID) has been received (step S905: YES), the CPU 21 references the memory device 23 and obtains patient information (step S906), then transmits the patient information to the measuring device 1 (step S907). Thus, just whose blood is the source of the analysis sample can be specified.

The controller 91 of the control board 9 of the measuring device 1 then determines whether the patient information has been received (step S916); when the controller 91 determines that the patient information has not been received (step S916: NO), the controller 91 enters the reception standby state. When the controller 91 determines that the patient information has been received (step S916: YES), the controller 91 controls the sample preparing section 41 to prepare a measurement sample, and thereafter starts the process of measuring the measurement sample (step S917). Specifically, DIFF measurement is executed, and electrical signals corresponding to the degree of the received side scattered light intensity and side fluorescent light intensity are transmitted to the control board 9 through the detection unit 5 and the analog processing unit 6. The A/D converter 92 of the control board 9 converts the received analog signals to 12-bit digital signals, and the operation unit 93 subjects the digital signals from the A/D converter 92 to predetermined processing, then sends the processed signals to the controller 91. The controller 91 transmits the received 12-bit integer sequence information as measurement data to the operation and display device 2 (step S918).

The CPU 21 determines whether the measurement data have been received (step S908); when the CPU 21 determines that the measurement data have been received (step S908: YES), the CPU 21 executes an analysis process based on the received measurement data (step S909). When the CPU 21 determines that the measurement data have not been received (step S908: NO), the CPU 21 enters the reception standby state.

Figure 10:
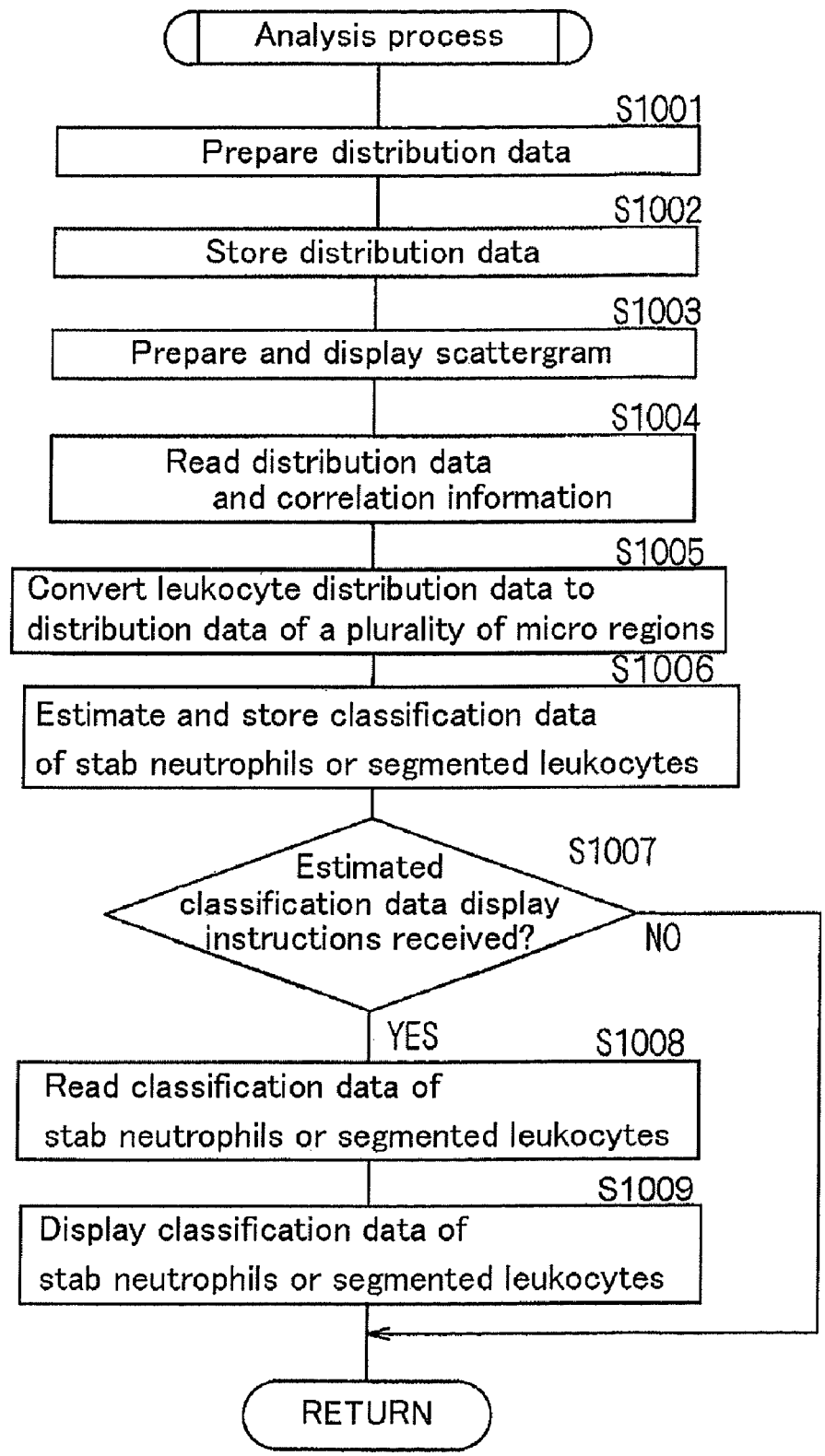
FIG. 10 is a flow chart showing the sequence of the analysis process performed by the CPU of the operation and display device of the first embodiment of the present invention.

FIG. 10 is a flow chart showing the sequence of the analysis process executed in step S909 of FIG. 9 by the CPU 21 of the operation and display device 2 of the first embodiment of the present invention. In FIG. 10, the CPU 21 of the operation and display device 2 prepares distribution data based on the received measurement data (step S1001), and associates the distribution data with the patient information and stores the data in the distribution data memory 231 of the memory device 23 (step S1002). The CPU 21 prepares a scattergram such as the one shown in FIG. 6, and displays the scattergram as the leukocyte classification results on the display device 25 (step S1003).

The CPU 21 reads the correlation information stored in the correlation information memory 233 and reads the distribution data stored in the distribution data memory 231 using the patient information as key information (step S1004), converts the distribution data to the distribution data of each of the plurality of micro regions (step S1005), estimates the stab neutrophil classification data or the segmented leukocyte classification data based on the converted distribution data and the correlation information and stores this information in the memory device 23 (step S1006). The CPU 21 determines whether a display instruction has been received for the estimated stab neutrophil classification information or the segmented leukocyte classification information (step S1007).

When the CPU 21 determines that the display instruction has not been received (step S2007: NO), the CPU 21 returns the process to step S910 of FIG. 9. When the CPU 21 determines that the display instruction has been received (step S1007: YES), the CPU 21 reads the stored stab neutrophil classification data or the segmented leukocyte classification data from the stab neutrophil/segmented leukocyte classification data memory 232 of the memory device 23 (step S1008), displays the data on the display device 25 (step S1009), and returns the process to step S910 of FIG. 9.

Returning now to FIG. 9, the CPU 21 determines whether a shutdown instruction has been received (step S910); when the CPU 21 determines that a shutdown instruction has not been received (step S910: NO), the CPU 21 returns the process to step S903, and the processes described above are repeated. When the CPU 21 determines that the shutdown instruction has been received (step S910: YES), the CPU 21 transmits the shutdown instruction information to the measuring device 1 (step S911).

The controller 91 of the control board 9 of the measuring device 1 determines whether shutdown instruction information has been received (step S919); when the controller 91 determines that the shutdown instruction information has not been received (step S919: NO), the controller 91 returns the process to step S913, and the processes described above are repeated. When the controller 91 determines that the shutdown instruction information has been received (step S919: YES), the controller 91 executes the shutdown (step S920) and the process ends.

Figure 11:
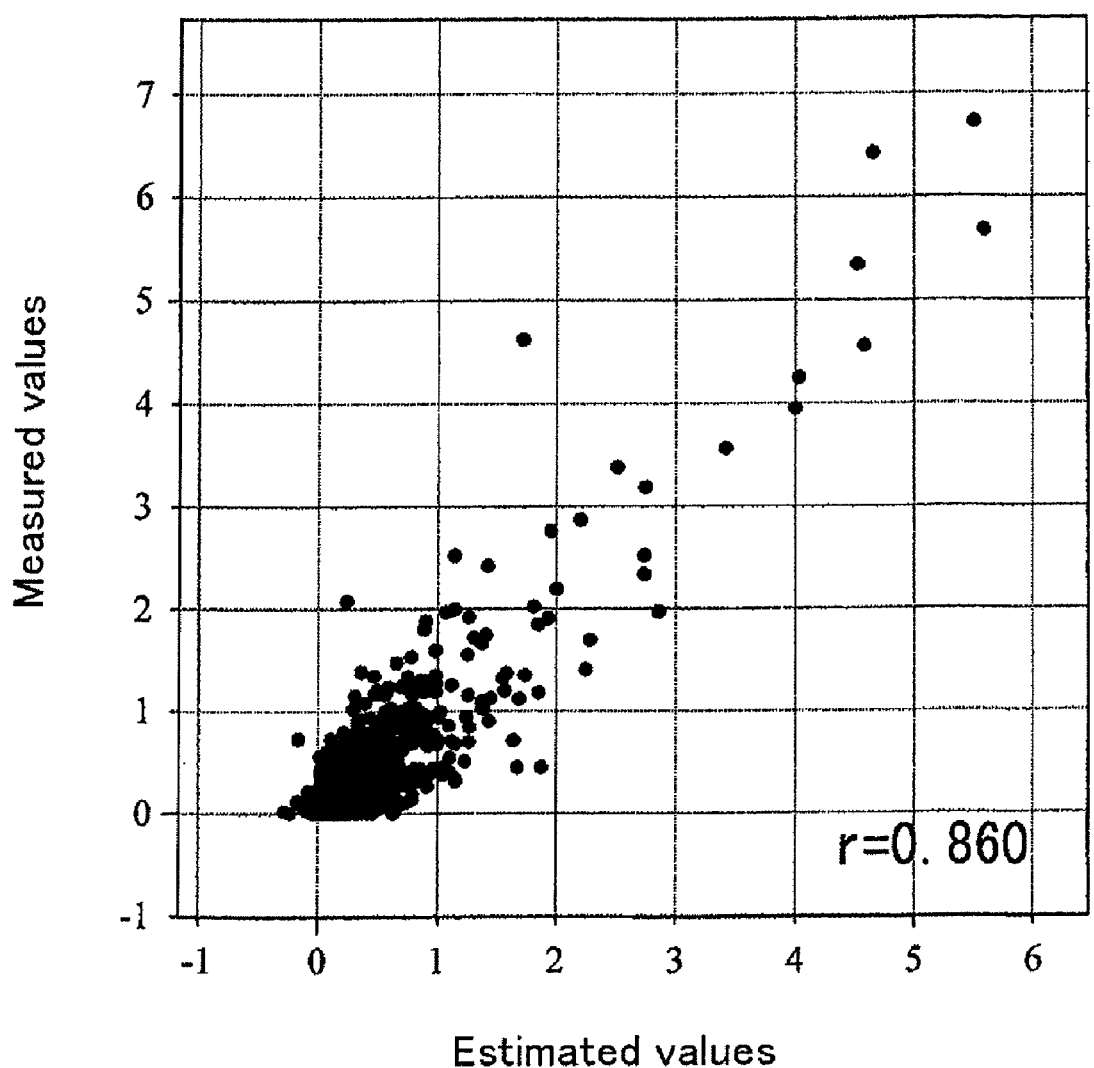
FIG. 11 is a graph showing the correlation between the predicted value and the measured value of the stab neutrophil.

FIG. 11 is a graph showing the correlation between the predicted value and the measured value of the stab neutrophil. In FIG. 11, the actual values measured by microscopic observation are plotted on the vertical axis and the estimated values are plotted on the horizontal axis by the blood cell analyzer of the first embodiment. The estimate value is estimated using multiple regression analysis functions determined by executing multiple regression analysis using the stab neutrophils as the objective variables and the distribution data of the micro regions as the explanatory variables when the scattergram distribution data (256×256) from the leukocyte DIFF measurement has been allocated to 32×32 micro regions. As shown in FIG. 11, the correlation coefficient r between the two has a high correlation of 0.860, which provides sufficient estimation precision.

Figure 12:
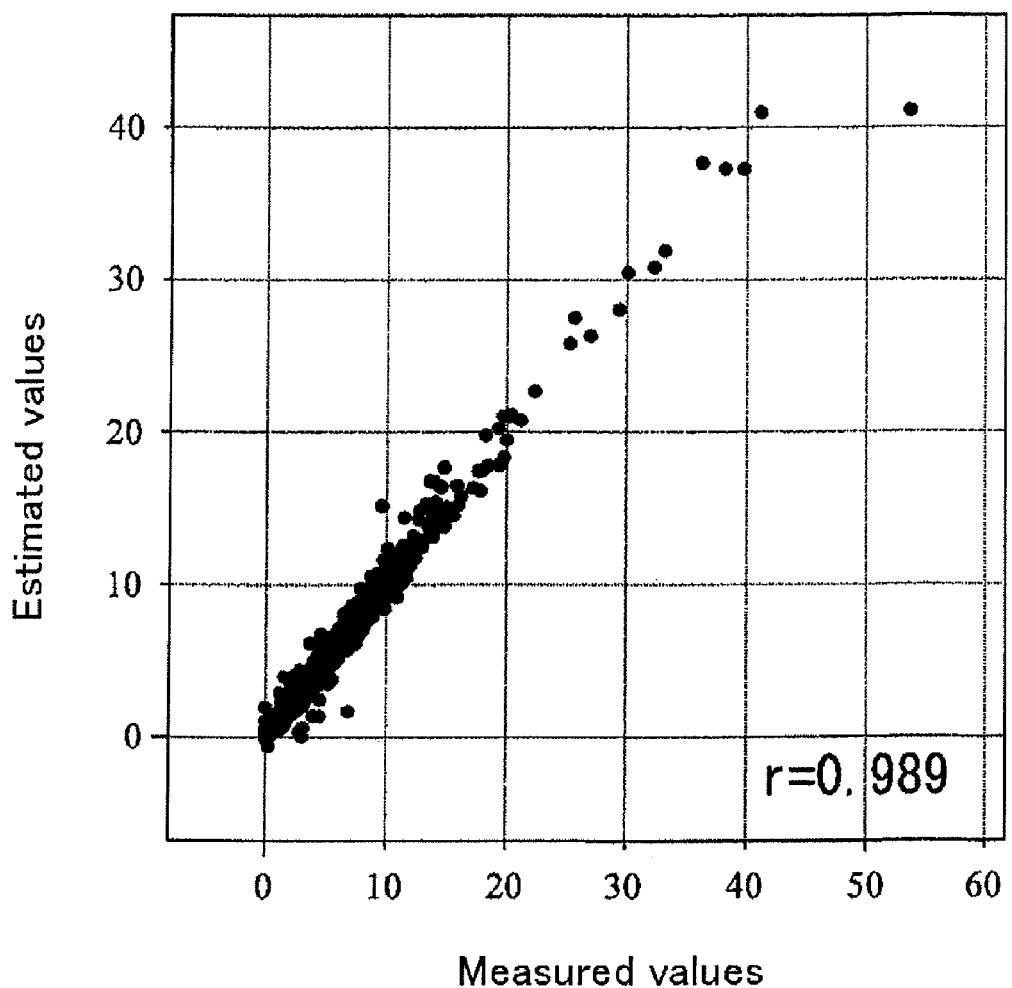
FIG. 12 is a graph showing the correlation between the estimated value and the measured value of the segmented leukocyte.

FIG. 12 is a graph showing the correlation between the estimated values and the measured values of the segmented leukocytes. In FIG. 12, the actual values measured by microscopic observation are plotted on the vertical axis and the estimated values are plotted on the horizontal axis by the blood cell analyzer of the first embodiment. The estimate value is also estimated using multiple regression analysis functions determined by executing multiple regression analysis using the segmented leukocytes as the objective variables and the distribution data as the explanatory variables when the single distribution datum of 256×256 channels of the leukocyte DIFF measurement is allocated to 32×32 micro regions which have 4×4 channels. As shown in FIG. 12, the correlation coefficient r between the two has an extremely high correlation of 0.989, which provides very high estimation precision.

Each correlation may also be determined by enhancing the characteristics of the distribution data via a characteristic enhancing filter, and classifying the enhanced distribution data at 5×5. In this way distribution data estimates of stab neutrophils or segmented leukocytes can be made with even greater precision. The result of single multiple regression analysis of the distribution data may be used, for example, as the characteristic enhancing filter.

According to the first embodiment described above, stab neutrophil or segmented leukocyte classification data can be estimated based on stored correlation information relating to unknown leukocyte distribution data by calculating and pre-storing correlation information between leukocyte distribution data obtained by the blood cell analyzer and classification information of either stab neutrophils or segmented leukocytes obtained externally from the blood cell analyzer. Therefore, it is possible to estimate, with excellent precision, the classification data of unmeasured stab neutrophil or segmented leukocyte just with the results of a conventional blood cell analyzer without the necessity of a separate apparatus or operational processing just to obtain classification data of the stab neutrophils or segmented leukocytes. Moreover, the onset of disease can be discovered at an early stage using such a simple and low cost blood cell analyzer.

(Second Embodiment)

The structure of the measuring device 1 of the second embodiment of the blood cell analyzer of the present invention is identical to the structure described in the first embodiment, hence, like parts are designated by like reference numbers and detailed description is omitted.

Figure 13:
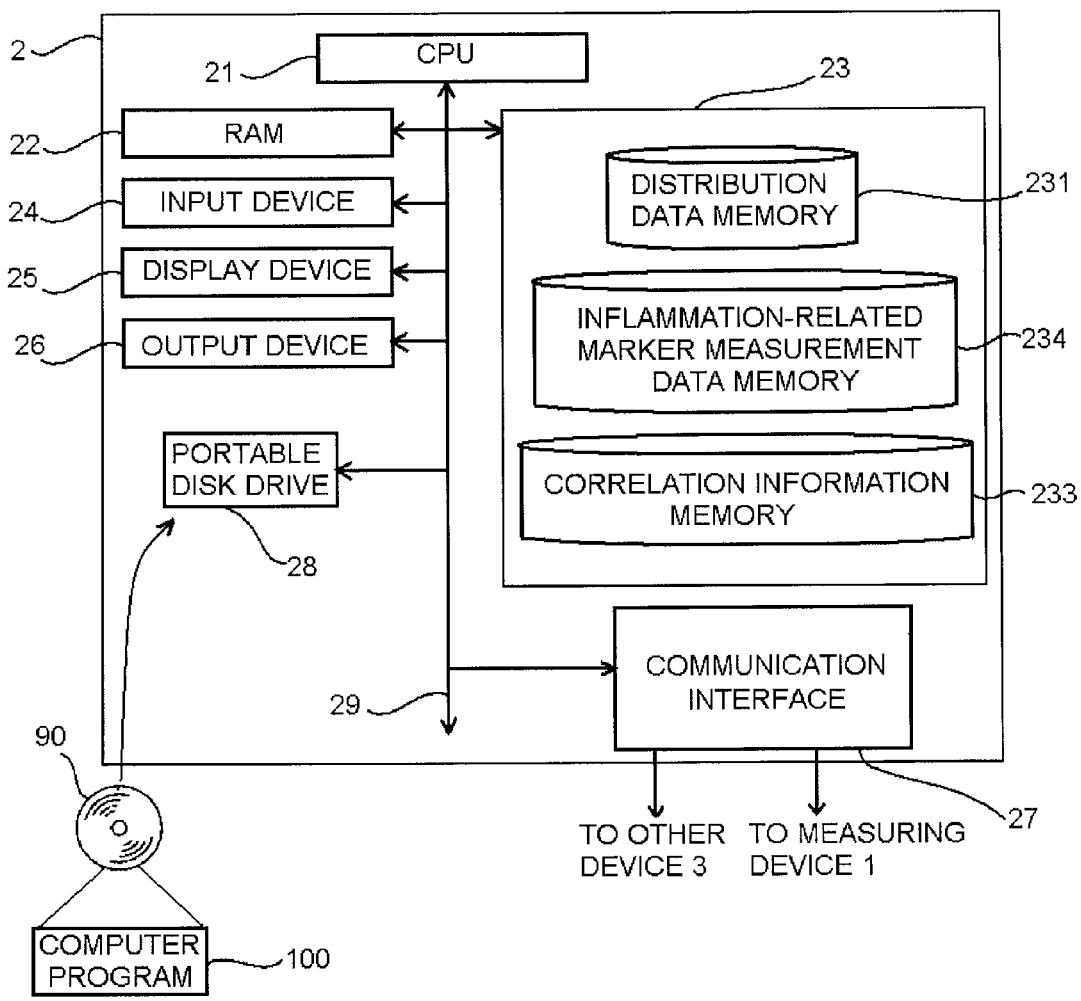
FIG. 13 is a block diagram showing the structure of the operation and display device of a second embodiment of the blood cell analyzer of the present invention.

FIG. 13 is a block diagram showing the structure of the operation and display device 2 of the second embodiment of the blood cell analyzer of the present invention.

The CPU 21, RAM 22, memory device 23, input device 24, display device 25, output device 26, communication interface 27, portable disk drive 28, internal bus 29, portable recording medium 90, and computer program 100 of the operation and display device 2 are identical to the first embodiment, hence, like parts are designated by like reference numbers and detailed descriptions are omitted. The distribution data memory 231 and the correlation information memory 233 of the memory device 23 are also identical to the first embodiment, and like parts are designated by like reference numbers. The second embodiment provides the memory device 23 with an inflammation-related marker measurement data memory 234. The structure of the memory device 23 is described below.

The memory device 23 is an internal fixed storage device (hard disk) or the like. The memory device 23 includes a distribution data memory 231 for storing the leukocyte distribution data obtained by the measuring device 1, inflammation-related marker measurement data memory 234 for storing the measurement data of inflammation-related markers obtained by another inspection device 3, and a correlation information memory 233 for storing correlation information relating to correlation relationships. The CPU 21 calculates the correlation information for estimating the measurement data of the inflammation-related markers from the leukocyte distribution data by analyzing the inflammation-related marker measurement data and the leukocyte distribution data respectively stored in the inflammation-related marker measurement data memory 234 and the distribution data memory 231. Note that the distribution data memory 231, inflammation-related marker measurement data memory 234, and correlation information memory 233 are not limited to being provided in the memory device 23 inasmuch as the necessary information may also be stored on an external computer and obtained via the communication interface 27. The correlation information may also be calculated by an external computer similarly provided with an operation and display device 2, and the calculated correlation information may also be pre-stored in the correlation information memory 233 of the memory device 23. In this case storing the distribution data and measurement data necessary for calculating the correlation information need not be stored in the memory device 23 of the operation and display device 2, and the process of calculating the correlation information by the CPU 21 may be omitted.

When the measuring device 1 and the operation and display device 2 of the blood cell analyzer of the above described structure measures the blood of a patient and has classified the leukocytes contained in the blood into lymphocytes, monocytes, eosinophils, neutrophils, basophils, a scattergram such as the one shown in FIG. 6 is prepared and displayed on the display device 25. The method for classifying the leukocytes used in the blood cell analyzer of the second embodiment of the present invention is identical to the first embodiment, and its description is therefore omitted.

The present inventors have discovered a high correlation between the leukocyte distribution data and the measurement data of inflammation-related markers by performing multiple regression analysis to extract the relationship between each type of disease and particle patterns of the leukocyte distribution data. Accordingly, the inflammation-relater marker measurement data can be estimated from the leukocyte distribution data by predetermining the correlation between the leukocyte distribution data obtained by a conventional blood cell analyzer and the measurement data of the inflammation-related markers obtained by another examination device.

The sequence for determining the correlation between the leukocyte distribution data and the inflammation-related marker measurement data is described below. Although the operation and display device 2 of the second embodiment is described in terms of calculating the correlation information relating to the correlation, the correlation information is not limited to calculation by the operation and display device 2 inasmuch as such correlation information may be calculated by an external computer and thereafter obtained over the network or via a portable recording medium.

Figure 14:
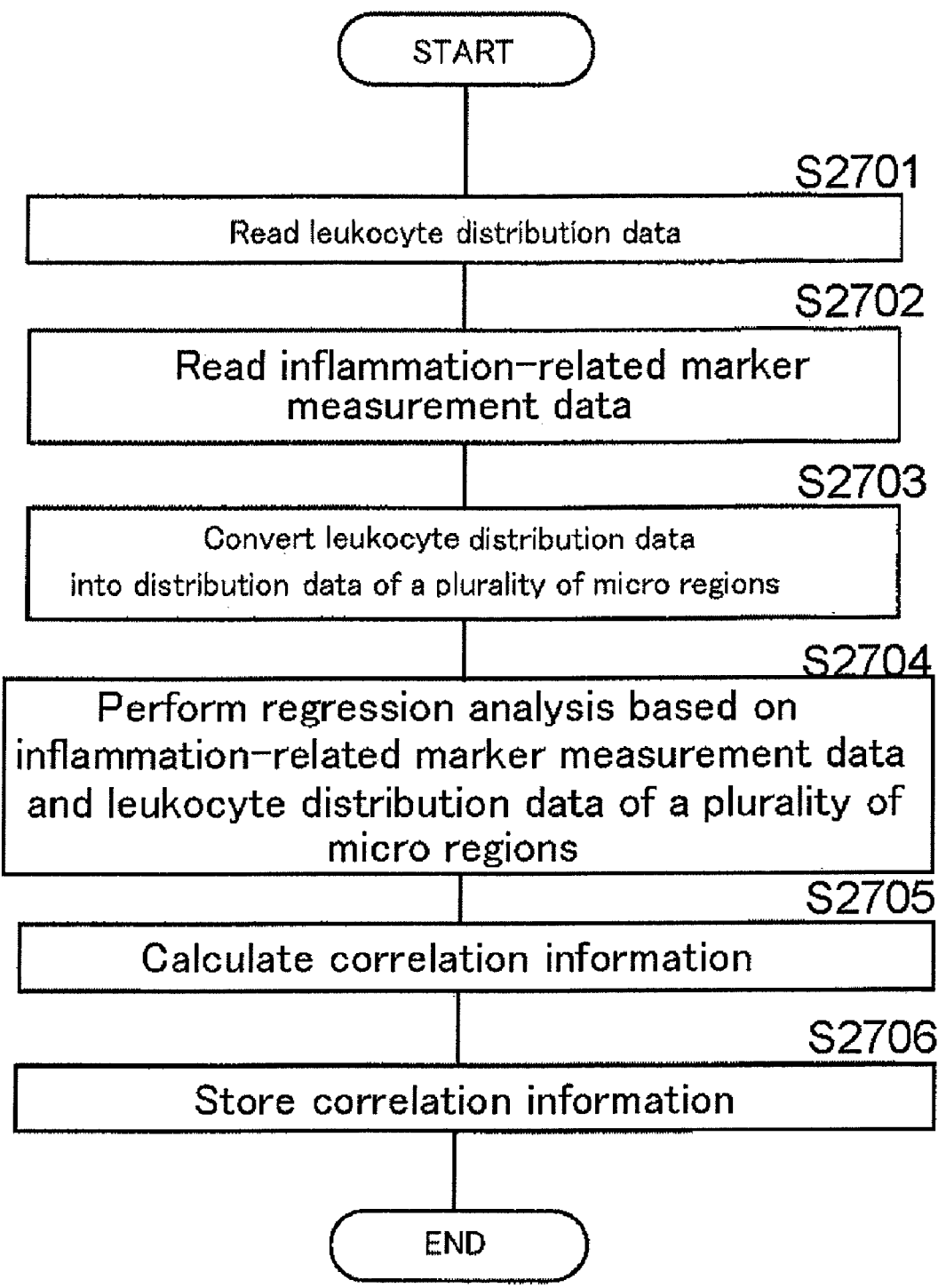
FIG. 14 is a flow chart showing the sequence of the process for calculating the correlation information relating to the correlation performed by the CPU of the operation and display device of the second embodiment of the present invention.

FIG. 14 is a flow chart showing a sequence of a process for calculating the correlation information relating to the correlation performed by the CPU 21 of the operation and display device 2 of the second embodiment of the present invention. The CPU 21 of the operation and display device 2 reads the leukocyte distribution data stored in the distribution data memory 231 of the memory device 23 (step S2701).

The CPU 21 reads the inflammation-related marker measurement data stored in the inflammation-related marker measurement data memory 234 of the memory device 23 (step S2702), and calculates the correlation information related to the correlation between the read leukocyte distribution data and the inflammation-related marker measurement data.

Figure 15:
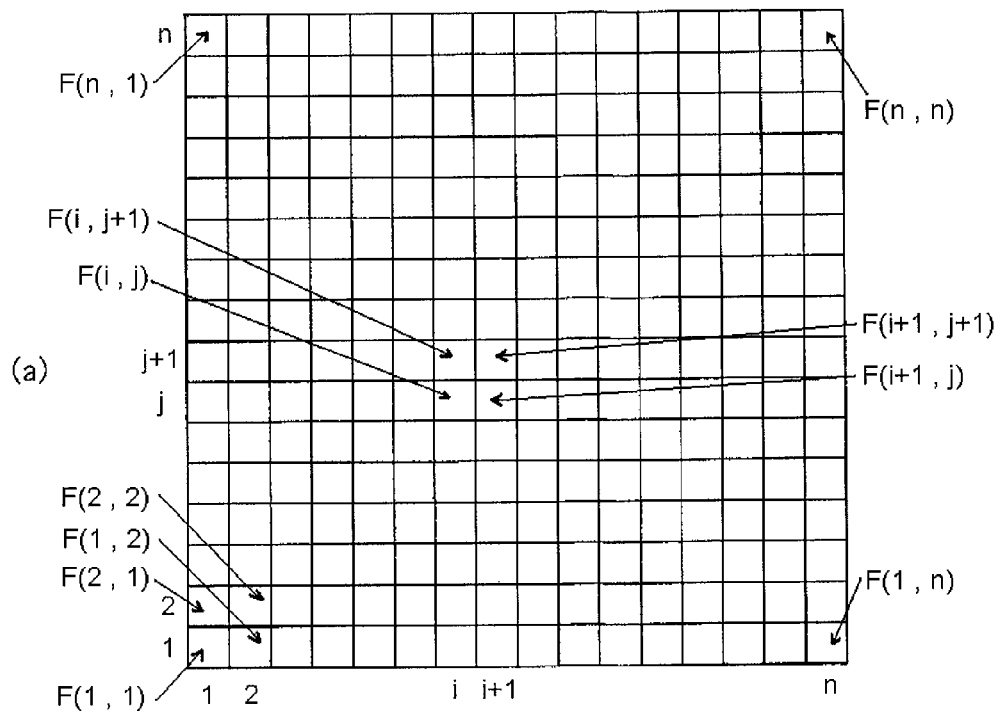
FIG. 15 illustrates the method of converting to distribution data of each small region based on the scattergram displaying the leukocyte distribution data.
Figure 15:
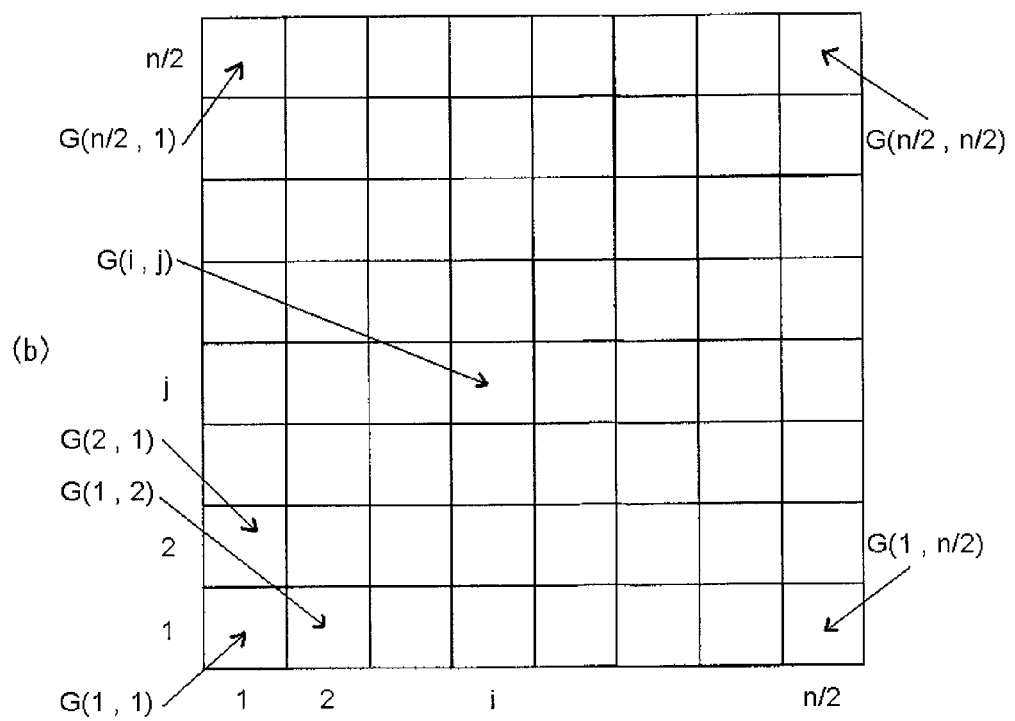

Specifically, the read leukocyte distribution data are converted to a distribution data for a plurality of micro regions (step S2703), multiple regression analysis is performed based on the converted distribution data of the micro regions and the read distribution data of the inflammation-related marker measurement data (step S2704), and the correlation information related to the relationship is calculated (step S2705). FIG. 15 illustrates the method of converting to distribution data of each micro region based on the scattergram displaying the leukocyte distribution data.

In the example of FIG. 15, the scattergram represents data groups in which a number F (i, j) is allocated to each n×n (n=256) address (i, j). The scattergram data may also be compressed when handling an excessive amount of data types. For example, when the addresses of the scattergram are converted so that four addresses become a single address (micro region), that is, the scattergram is compressed to n/2× n/2, the number G (i, j) of the addresses of the compressed scattergram can be expressed as shown in equation (10).

$$G(1, 1) = F(1, 1) + F(1, 2) + F(2, 1) + F(2, 2) \quad \text{Equation (10)}$$

$$G(1, 2) = F(1, 3) + F(1, 4) + F(2, 3) + F(2, 4)$$

$$\vdots$$

$$G(i, j) = \begin{matrix} F(2i-1, 2j-1) + \\ F(2i-1, 2j) + \\ F(2i, 2j-1) + F(2i, 2j) \end{matrix}$$

$$\vdots$$

$$G(i, j) = \begin{matrix} F(n-1, n-1) + \\ F(n-1, n) + \\ F(n, n-1) + F(n, n) \end{matrix}$$

For example, when an inflammation reaction occurs in vivo due to disease, the ratio of immature leukocytes increases, segmented leukocytes with few segmented nuclei and stab neutrophils with unsegmented nuclei also increase. In this way the number of data can be compressed, and correlation information can be more efficiently calculated by converting the original distribution data to distribution data of micro regions configured by four addresses.

When the 256×256 distribution data are compressed to 32×32 distribution data and subjected to multiple regression analysis, the CPU 21 calculates the multiple regression function h of the distribution data xki (i−1, 2, . . . s) of a plurality of micro regions and the measurement data Ck of the inflammation-related markers using the distribution data xki (i=1, 2, . . . s) (s=1024) of a plurality of micro regions converted from the leukocyte distribution data Xk (k=1, 2, . . . n) as explanatory variables, and the measurement data Ck of the inflammation-related markers as objective variables. When the distribution data xi has been obtained by the CPU 21 for each micro region by converted from the new leukocyte distribution data X by calculating the multiple regression analysis function h as the correlation information, the CPU 21 can then calculate the estimated data of the inflammation-related markers via equation (11).

$$B = g(x1, x2, \ldots, xi, \ldots, xs) \qquad \text{Eq. (11)}$$

Of course, linear multiple regression analysis may also be executed assuming the existence of a linear correlation between the obtained inflammation-related marker measurement data Ck and the distribution data xki (i=1, 2, ... s) of a plurality of micro regions converted from the leukocyte distribution data Xk (k=1, 2, ... n). In this case, the CPU 21 calculates multiple regression functions c0, ci as the correlation information by executing linear multiple regression analysis using the distribution data xki (i=1, 2, ... s) of a plurality of micro regions converted from the leukocyte distribution data Xk (k=1, 2, ... n) as explanatory variables, and the obtained inflammation-related marker measurement data Ck as objective variables. When the distribution data xi has been obtained by the CPU 21 for each micro region by converted from the new leukocyte distribution data X by calculating the multiple regression analysis functions c0 and ci, the CPU 21 can then calculate the estimated measurement data C of the inflammation-related markers via equation (12).

$$C = \sum_{i=1}^{s} ci \cdot xi + c0$$

Equation (12)

The CPU 21 stores the calculated correlation information in the correlation information memory 233 of the memory device 23 (step S2706).

Note that the obtained leukocyte distribution data may also be classified into a plurality of categories, so that correlation information can also be stored which relates to the correlation between the inflammation-related marker measurement data and distribution data for each classified category. Inflammation-related marker measurement data can also be estimated with higher precision by calculating and storing correlation information based on categories representing a high correlation between the distribution data and the inflammation-related marker measurement data.

The flow chart showing the sequence of the processing performed by the CPU 21 of the operation and display device 2 and the controller 91 of the control board 9 of the measuring device 1 of the second embodiment of the present invention is identical to FIG. 9 of the first embodiment with the exception of the sequence of the analysis process executed in step S909 of FIG. 9, hence, like parts are designated by like reference numbers and detailed description is abbreviated.

Figure 16:
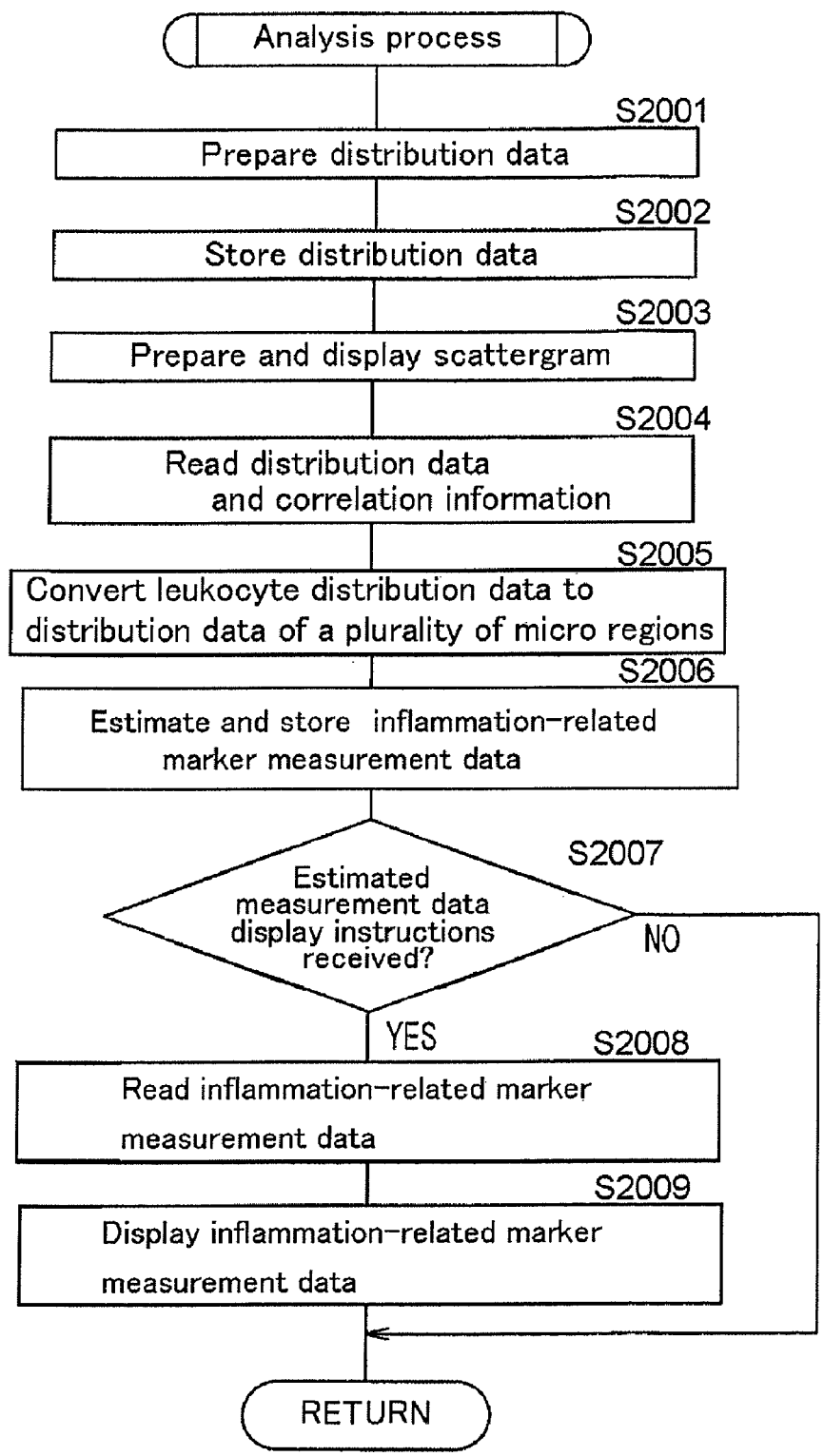
FIG. 16 is a flow chart showing the sequence of the analysis process performed by the CPU of the operation and display device of the second embodiment of the present invention.

FIG. 16 is a flow chart showing the sequence of the analysis process executed in step S909 of FIG. 9 by the CPU 21 of the operation and display device 2 of the second embodiment of the present invention. In FIG. 16, the CPU 21 of the operation and display device 2 prepares distribution data based on the received measurement data (step S2001), and associates the distribution data with patient information and stores the data in the distribution data memory 231 of the memory device 23 (step S2002). The CPU 21 prepares a scattergram such as the one shown in FIG. 6, and displays the scattergram as the leukocyte classification results on the display device 25 (step S2003).

The CPU 21 reads the correlation information stored in the correlation information memory 233 and reads the distribution data stored in the distribution data memory 231 using the patient information as key information (step S2004), converts the distribution data to distribution data of each of a plurality of micro regions (step S2005), estimates the inflammation-related marker measurement data based on the converted distribution data and the correlation information and stores this information in the inflammation-related marker measurement data memory 234 of the memory device 23 (step S2006). The CPU 21 determines whether a display instruction for the estimated inflammation-related marker measurement data has been received (step S2007).

When the CPU 21 determines that the display instruction has not been received (step S2007: NO), the CPU 21 returns the process to step S910 of FIG. 9. When the CPU 21 determines that the display instruction has been received (step S2007: YES), the CPU 21 reads the measurement data of the inflammation-related marker (for example, CRP) from the inflammation-related marker measurement data memory 234 (step S2008), displays the information on the display device 25 (step S2009), and returns the process to step S910 of FIG. 9.

Note that when storing the correlation information relating to the correlation between the distribution data and the inflammation-related marker measurement data for each of the classified leukocyte distribution data, a process is required for classifying the distribution data into a plurality of categories using the blood cell analyzer. In this way the inflammation-related marker measurement data can be estimated using the correlation information corresponding to the classified category. A self-assembly map or like method may be used as the method of classifying the distribution data into a plurality of categories.

Figure 17:
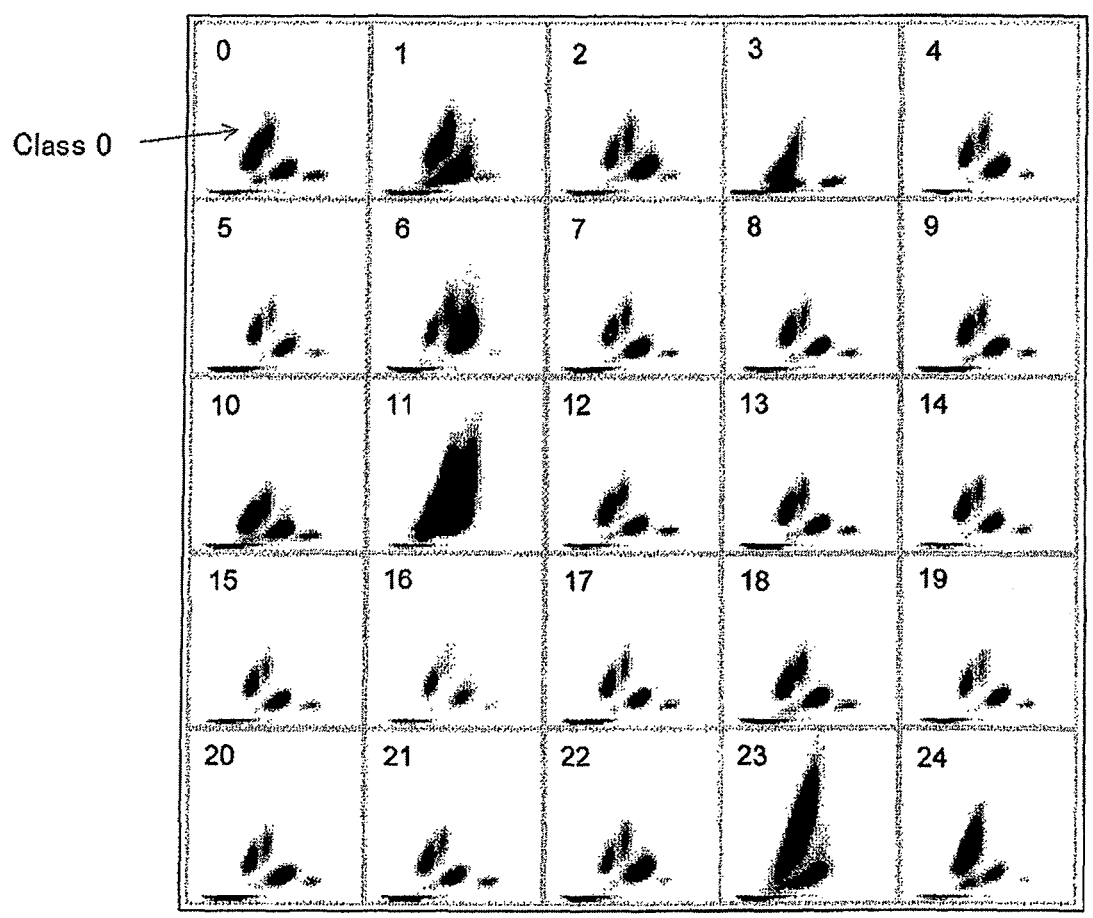
FIG. 17 shows an example of a leukocyte distribution diagram with 5×5 classifications using self-assemble map using C reactive proteins (CRP) as an inflammation-related marker.

FIG. 17 shows an example of a leukocyte distribution diagram with 5×5 categories classified using a self-assemble map using C reactive proteins (CRP) as an inflammation-related marker. In the example of FIG. 17, the top level holds class 0, class 1, class 2, class 3, and class 4 from left to right; the next lower level holds class 5, class 6 and the like from left to right; the bottom level holds class 20, class 21, class 22, class 23, and class 24 from left to right. In the example, class 8 is considered as a group containing mostly normal specimens and specimens with a low degree of inflammation; class 6 is considered a group containing mostly specimens with a high degree of inflammation.

Figure 18:
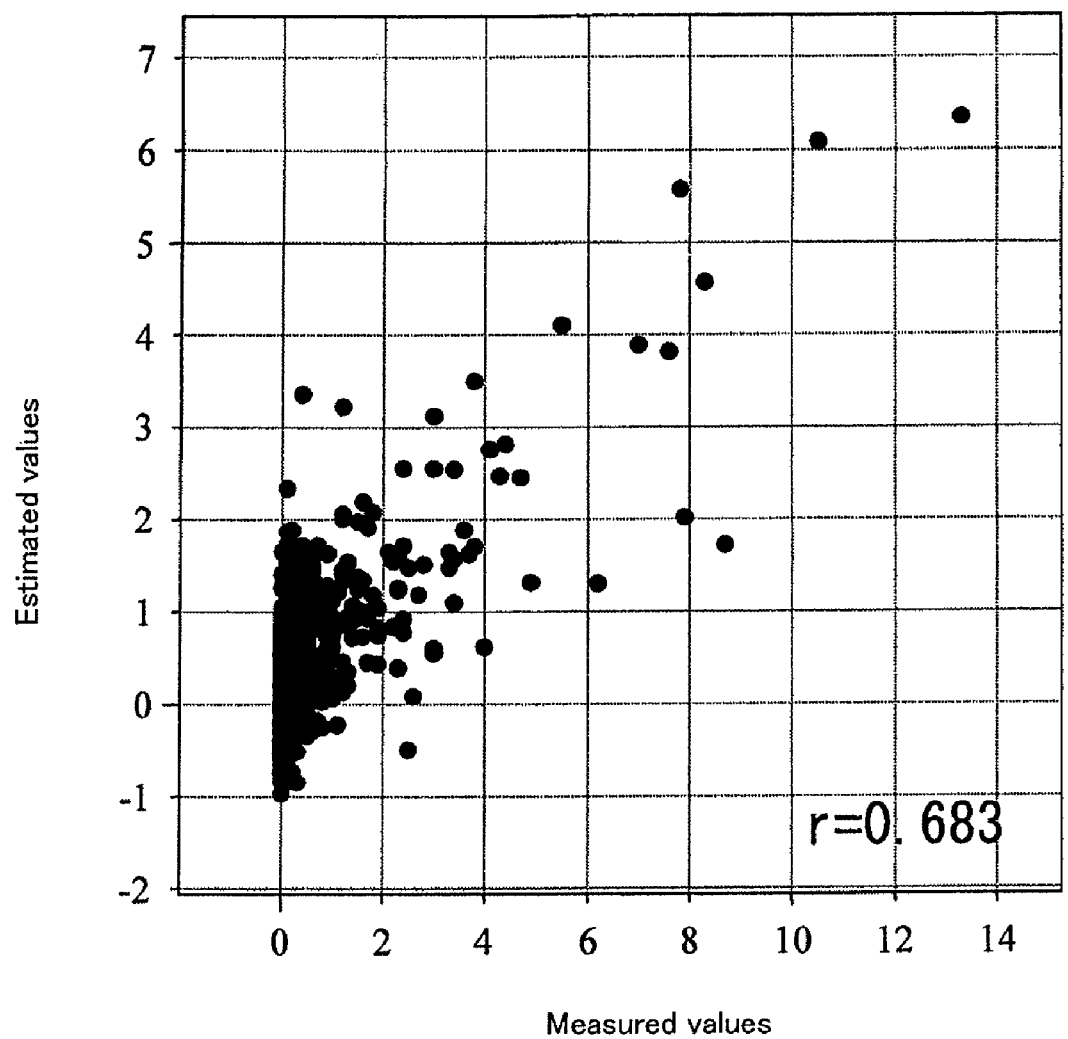
FIG. 18 is a graph showing the correlation between the estimated value and the measured value of CRP in class 8.
Figure 19:
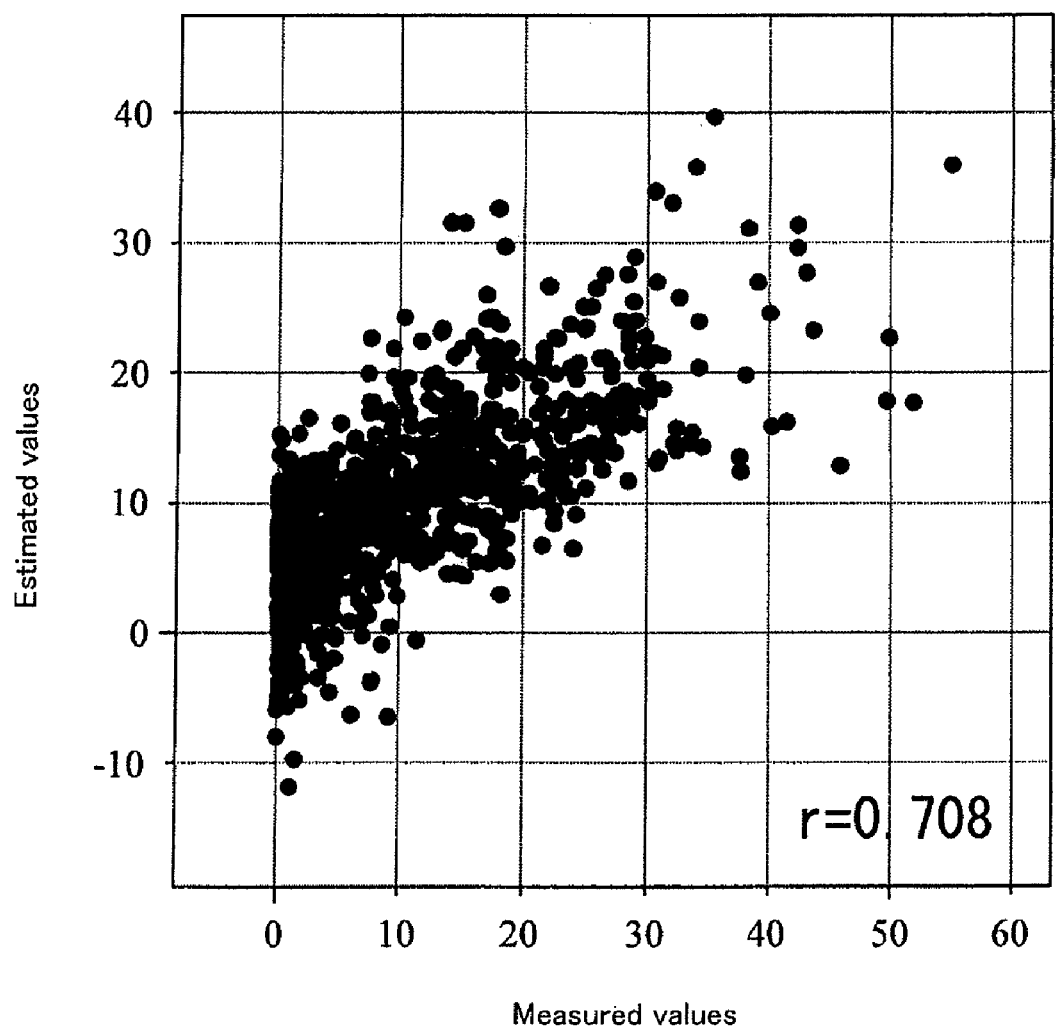
FIG. 19 is a graph showing the correlation between the estimated value and the measured value of CRP in class 6.

FIGS. 18 and 19 are graphs respectively showing the correlation between the estimated value and the measured value of CRP in classes 8 and 6. In FIGS. 18 and 19, the estimated values obtained by the blood cell analyzer of the second embodiment are plotted on the vertical axis and the measured values are plotted on the horizontal axis. The estimate value is also estimated using multiple regression analysis functions determined by executing multiple regression analysis using the stab neutrophils as the objective variables and the distribution data as the explanatory variables when the single distribution datum of 256×256 channels of the leukocyte DIFF measurement is allocated to 32×32 micro regions which have 4×4 channels. As shown in FIGS. 18 and 19, the correspondence coefficients between the two are respectively 0.683 and 0.708, indicating a high correspondence between the estimated value and the measured value, which has been confirmed to be useful as clinical exam information.

Figure 20:
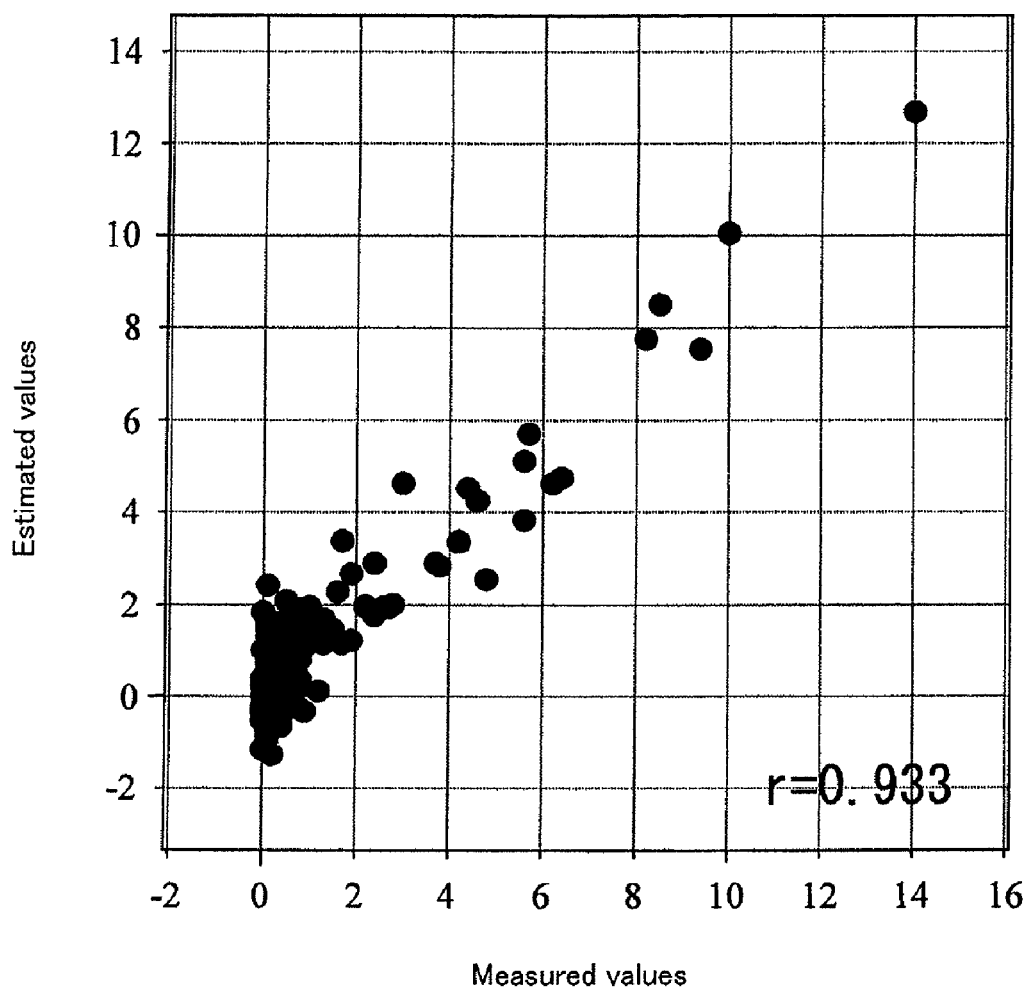
FIG. 20 is a graph showing the correlation between the estimated value and the measured value of CRP in class 8 after 4 to 7 days.
Figure 21:
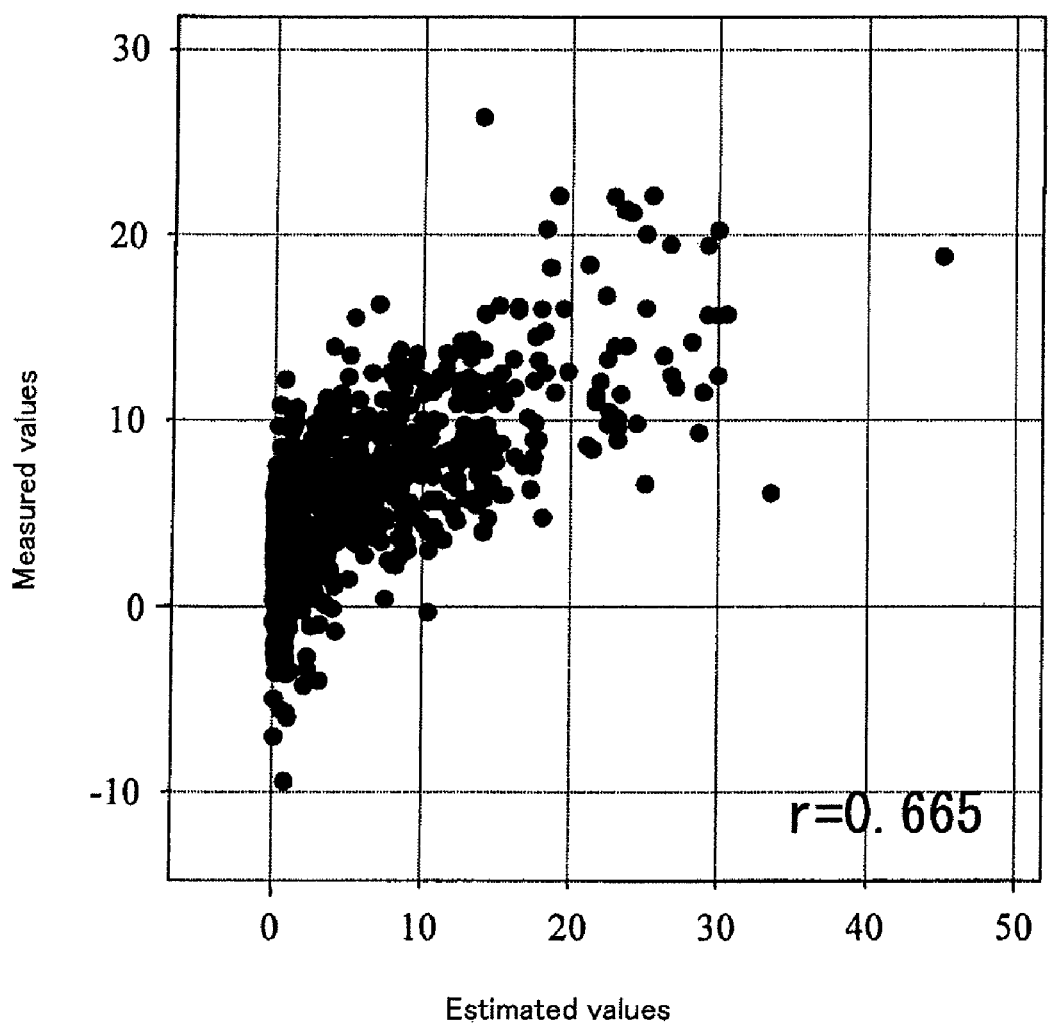
FIG. 21 is a graph showing the correlation between the estimated value and the measured value of CRP in class 6 after 4 to 7 days.

The CRP measurement data can also be estimated after several days from the current leukocyte distribution data by using the correlation obtained by multiple regression analysis of the leukocyte distribution data of a certain time point and the CRP measurement data obtained several days later. FIGS. 20 and 21 are graphs respectively showing the correlation between the estimated value and the measured value of CRP 4 to 7 days later in classes 8 and 6. In FIG. 20, the estimated values obtained by the blood cell analyzer of the second embodiment are plotted on the vertical axis and the measured values are plotted on the horizontal axis. In FIG. 21, the estimated values obtained by the blood cell analyzer of the second embodiment are plotted on the vertical axis and the measured values are plotted on the horizontal axis.

As shown in FIGS. 20 and 21, the correlation coefficients r between the two are 0.933 and 0.665, respectively, which suggests it may be possible to estimate a CRP value after several days.

Each correlation may also be determined by enhancing the characteristics of the distribution data via a characteristic enhancing filter, and classifying the enhanced distribution data at 5×5. In this way distribution data estimates of stab neutrophils or segmented leukocytes can be made with even greater precision. The result of single regression analysis of the distribution data may be used, for example, as the characteristic enhancing filter.

According to the second embodiment described above, the measurement data of an inflammation-related marker can be estimated based on stored correlation information relative to unknown leukocyte distribution data by calculating and pre-storing the correlation information between the leukocyte distribution data obtained by the blood cell analyzer and the measurement data of the inflammation-related marker obtained from another blood cell analyzer. Therefore, the inflammation-related marker measurement data which is not the measurement object can be estimated from only the result of the conventional blood cell analyzer without requiring a separate apparatus, reagents and the like to obtain the measurement data of the inflammation-related marker. Moreover, the onset of disease can be discovered at an early stage using such a simple and low cost blood cell analyzer.

Note that although the analysis results are displayed by the display device 25 of the operation and display device 2 in the second embodiment described above, the present invention is not specifically limited to this arrangement inasmuch as the analysis results may also be displayed on a display device of another computer connected to the network.

The present invention is not limited to the above embodiments and may be variously modified and parts replaced insofar as such modifications are within the scope of the claims of the invention. For example, the inflammation-related marker may be a C-reactive protein, serum amyloid A, or erythrocyte sedimentation rate; when the inflammation-related marker is C-reactive protein, the measurement data of the inflammation-related marker may be measurement data of the C-reactive protein obtained after a predetermined number of days have elapsed.

The invention claimed is:

1. A blood cell analyzer comprising:
 a detector for detecting first and second light information from leukocytes contained in a specimen of a subject; and
 a controller, including a memory under the control of a processor, the memory storing:
  correlation information relating to the correlation between inflammation-related marker measurement data and leukocyte distribution data; and
  instructions enabling the processor to carry out operations, comprising:
   (a) generating leukocyte distribution data for classifying the leukocytes to subclasses, the leukocyte distribution data including a two dimensional distribution on which the leukocytes in the specimen are plotted according to the detected first and second light information;
   (b) obtaining the inflammation-related marker measurement data based on the correlation information and the leukocyte distribution data of the subject; and
   (c) outputting the obtained inflammation-related marker measurement data.

2. The blood cell analyzer of claim 1, wherein the operations further comprise:
 (d) classifying the leukocyte distribution data in a plurality of categories; and
 (e) storing, in the memory, the correlation information of the inflammation-related marker measurement data and the distribution data of the leukocytes classified in the plurality of categories.

3. The blood cell analyzer of claim 2, wherein the operations further comprise:
 (f) classifying the leukocyte distribution data in a plurality of categories; and
 wherein step (b) comprises obtaining the inflammation-related marker measurement data based on the correlation information and the distribution data classified in the plurality of categories.

4. The blood cell analyzer of claim 3, wherein
 the correlation information is a multiple regression function h of the inflammation-related marker measurement data Ck and the distribution data xki (1=1, 2, ... s) of the plurality of micro regions, calculated based on the obtained inflammation-related marker measurement data Ck and the distribution data xki (i=1, 2, ... s) of a plurality of micro regions converted from the leukocyte distribution data Xk (k=1, 2, ... n); and
 step (b) comprises calculating, via equation (3), the obtained measurement data of the inflammation-related marker based on the multiple regression function h and the micro region distribution data xi converted from the leukocyte distribution data of the subject.

$$B = g(x1, x2, \ldots, xi, \ldots, xs) \quad \text{Eq. (3)}$$

5. The blood cell analyzer of claim 3, wherein
 the correlation information is multiple regression functions c0 and ci calculated by executing linear multiple regression analysis based on the obtained inflammation-related marker measurement data Ck and the distribution data xki (i=1, 2, ... s) of the plurality of micro regions converted from the leukocyte distribution data Xk (k=1, 2, ... n); and
 step (b) comprises calculating, via equation (4), the obtained measurement data of the inflammation-related marker based on the multiple regression functions co and ci and the distribution data xi of the plurality of micro regions converted form the leukocyte distribution data X of the subject $$C = \sum_{i=1}^{s} ci \cdot xi + c0 \qquad \text{Equation (4)}$$

6. The blood cell analyzer of claim 1, wherein
 the inflammation-related marker is any among c-reactive protein, serum amyloid A, and reticulocyte sedimentation rate.

7. The blood cell analyzer of claim 1, wherein
 the inflammation-related marker is c-reactive protein, and the obtained measurement data of the inflammation-related marker are measurement data of the c-reactive protein after several days have elapsed.

8. The blood cell analyzer of claim 1, wherein the step (b) comprises:
 (d) dividing the two dimensional distribution into a plurality of regions;
 (e) converting the distribution of plots in each of the regions into values; and (f) applying the values with a predefined function which defines a relationship of the values and the inflammation-related marker measurement data.

9. The blood cell analyzer of claim 1, further comprising a sample preparing section which prepares a specimen containing a fluorescence dye and a blood sample.

10. The blood cell analyzer of claim 9, wherein the detector is configured to irradiate leukocytes with light and to detect scattered light and fluorescence from the leukocytes, and wherein the first light information is an intensity of the detected scattered light and the second light information is an intensity of the detected fluorescence.

11. A blood cell analyzing method comprising:
(a) generating leukocyte distribution data for classifying leukocytes to subclasses, the leukocyte distribution data including a two dimensional distribution on which the leukocytes in a specimen are plotted according to first and second light information which is detectable from leukocytes;
(b) obtaining inflammation-related marker measurement data based on correlation information and the leukocyte distribution data, the correlation information relating to the correlation between inflammation-related marker measurement data and the leukocyte distribution data; and
(c) outputting the obtained inflammation-related marker measurement data.

12. A computer program product, comprising:
a computer readable medium; and
instructions, on the computer readable medium, adapted to enable a general purpose computer to perform operations, comprising:
(a) generating leukocyte distribution data for classifying leukocytes to subclasses, the leukocyte distribution data including a two dimensional distribution on which the leukocytes in a specimen are plotted according to first and second light information which is detectable from leukocytes;
(b) obtaining inflammation-related marker measurement data based on correlation information and leukocyte distribution data, the correlation information relating to the correlation between inflammation-related marker measurement data and the leukocyte distribution data; and
(c) outputting the obtained inflammation-related marker measurement data.

* * * * *

UNITED STATES PATENT AND TRADEMARK OFFICE
CERTIFICATE OF CORRECTION

| | |
|---|---|
| PATENT NO. | : 8,349,256 B2 |
| APPLICATION NO. | : 12/622804 |
| DATED | : January 8, 2013 |
| INVENTOR(S) | : Hiromi Kataoka et al. |

Page 1 of 1

It is certified that error appears in the above-identified patent and that said Letters Patent is hereby corrected as shown below:

On the Title Page

Item (73), immediately after "Sysmex Corporation, Kobe (JP)", insert --; Kochi University, Kochi (JP)--.

Signed and Sealed this
Third Day of December, 2013

Margaret A. Focarino
*Commissioner for Patents of the United States Patent and Trademark Office*